United States Patent
Rehberger et al.

(10) Patent No.: US 8,021,654 B2
(45) Date of Patent: Sep. 20, 2011

(54) METHODS OF TREATING PIGS WITH BACILLUS STRAINS

(75) Inventors: Thomas Rehberger, Wauwatosa, WI (US); Mari Ellen Davis, Waukesha, WI (US); Ashley Baker, Waukesha, WI (US)

(73) Assignee: Danisco A/S, Copenhagen (DK)

( * ) Notice: Subject to any disclaimer, the term of this patent is extended or adjusted under 35 U.S.C. 154(b) by 191 days.

(21) Appl. No.: 12/404,149

(22) Filed: Mar. 13, 2009

(65) Prior Publication Data
US 2009/0280090 A1 Nov. 12, 2009

Related U.S. Application Data

(60) Provisional application No. 61/036,741, filed on Mar. 14, 2008.

(51) Int. Cl.
A01N 63/00 (2006.01)

(52) U.S. Cl. .................... 424/93.3; 424/93.46; 424/93.1

(58) Field of Classification Search .................. None
See application file for complete search history.

(56) References Cited

U.S. PATENT DOCUMENTS

| | | | |
|---|---|---|---|
| 2,906,622 A | 9/1959 | Lewis | |
| 2,942,977 A | 6/1960 | Lewis | |
| 3,892,846 A | 7/1975 | Wortham | |
| 4,820,531 A | 4/1989 | Tomes | |
| 4,919,936 A | 4/1990 | Iwanami | |
| 5,073,367 A * | 12/1991 | Nguyen | 424/93.462 |
| 5,478,557 A | 12/1995 | Nisbet | |
| 5,482,723 A | 1/1996 | Sasaki | |
| 5,507,250 A | 4/1996 | Reddy | |
| 5,540,924 A | 7/1996 | Onishi | |
| 5,703,040 A | 12/1997 | Landolo | |
| 5,718,894 A | 2/1998 | Mann | |
| 5,830,993 A | 11/1998 | Biecha | |
| 5,840,318 A | 11/1998 | Marshall | |
| 5,879,719 A | 3/1999 | Valentine | |
| 5,945,333 A | 8/1999 | Rehberger | |
| 5,964,187 A | 10/1999 | Willis | |
| 5,965,128 A | 10/1999 | Doyle | |
| 6,008,195 A | 12/1999 | Selsted | |
| 6,156,355 A | 12/2000 | Shields, Jr. | |
| 6,207,411 B1 | 3/2001 | Ross | |
| 6,221,650 B1 | 4/2001 | Rehberger | |
| 6,346,422 B1 | 2/2002 | Butty | |
| 6,410,016 B2 | 6/2002 | Maruta | |
| 7,247,299 B2 | 7/2007 | Lin et al. | |
| 7,618,640 B2 * | 11/2009 | Rehberger et al. | 424/200.1 |
| 7,754,469 B2 | 7/2010 | Baltzley et al. | |
| 2002/0018770 A1 | 2/2002 | Maruta | |
| 2003/0099624 A1 | 5/2003 | Porubcan | |
| 2004/0170617 A1 | 9/2004 | Finegold | |
| 2005/0255092 A1 | 11/2005 | Rehberger | |
| 2006/0067924 A1 | 3/2006 | Lee et al. | |
| 2007/0202088 A1 * | 8/2007 | Baltzley et al. | 424/93.46 |
| 2009/0275109 A1 | 11/2009 | Bellot et al. | |

FOREIGN PATENT DOCUMENTS

| | | |
|---|---|---|
| WO | 20040104175 | 12/2004 |
| WO | WO 2005/112658 | * 12/2005 |

OTHER PUBLICATIONS

Hofacre, C L et al, "Subcutaneous Clostridial infection in broilers," Case Report, Avian Diseases vol. 30(3):620-622, 1986.
Hong, H. A. et al, "The use of bacterial spore formers as probiotics," FEMS Microbiol. Rev. (2005) 29:813-835.
Hungate, R. E. et al, "Microbiological and physiological changes associated with acute indigestion in sheep," Cornell Vet. (1952) 42:423.
Janstova, B. et al, "Heat Resistance of *Bacillus* spp. Spores Isolated form Cow's Milk and Farm Environment," ACTA VET.. BRNO (2001) 70:179-184.
Jenny, B. F. et al, "Performance and fecal flora of calves fed a *Bacillus subtilis* concentrate," J. Dairy Sci. (1991) 74:1968-1973.
Jost B. H. et al, "Atypical cpb2 genes, encoding beta2-toxin in *Clostridium perfringens* isolates of nonporcine origin," Infect. Immun. (2005) 73:652-656.
Karunakaran, D et al, "Use of antibiotics and its impact on gut microflora in turkeys," Am Avian Path, Philadelphia, PA, Aug. 2004.
Karunakaran, D, "Microbioligical challenges of commercial turkey flocks and methods of control," Poster #PP51 presented at AAAP Symposium on Poultry Vaccines and Vaccination Practices, Jul. 15-17, 2002.
Kennedy, C et al, "The A-toxin of *Clostridium septicum* is essential for virulence," Molecular Microbiology, 57(5): 1357-1366, 2005.
King, M. et al, "Terminal restriction fragment length polymorphism analysis of gastrointestinal bacteria from conventional and segregated early weaned pigs: colonization and succession of putative pathogens and potential direct fed microbials," J. Anim Sci. (2005) 83 (Suppl. 1): 197.
Kyriakis, S. C. et al, "The effect of probiotic LSP 122 on the control of post-weaning diarrhea syndrome of piglets," Res. Vet. Sci. (1999) 67:223-228.
La Ragione R M et al, "*Bacillus subtilis* spores competitively exclude *Escherichia coli* 078:K80 in poultry," Vet Microbiol 79:133-142, 2001.
La Ragione, R. M. et al, "Competitive exclusion by *Bacillus subtilis* spores of *Salmonella enterica* serotype Enteritidis and *Clostridium perfringens* in young chickens," Vet. Microbiol, (2003) 94:245-256.
Lu, J et al, "Diversity and succession of the intestinal bacterial community of the maturing broiler chicken," Applied and Environmental Microbiology, 69(11):6816-6824, Nov. 2003.
Marquardt, R et al, "Passive protective effect of egg-yolk antibodies against enterotoxigenic *Escherichia coli* K88+ infection in neonatal and early-weaned piglets," FEMS Immunology and Med Microbiology 23:283-288, 1999.
Marsh, T. et al, "Terminal restriction fragment length polymorphism analysis web-based research tool for microbial community analysis," Appl Environ Microbiol (2000) 66:3616-3620.

(Continued)

Primary Examiner — Vera Afremova
(74) Attorney, Agent, or Firm — Whyte Hirschboeck Dudek S.C.

(57) ABSTRACT

Disclosed are methods of administering at least two *Bacillus* strains to a pig, such as female breeding stock, nursery pigs, or other pigs. The *Bacillus* strains inhibit *Clostridium* in litters borne to the pig. The *Bacillus* strains also are useful when administered to herds lacking symptoms of *Clostridium* infection. Administration of the *Bacillus* strains improves performance of female breeding stock and in piglets borne by the female breeding stock.

23 Claims, 4 Drawing Sheets

OTHER PUBLICATIONS

Figure 1:
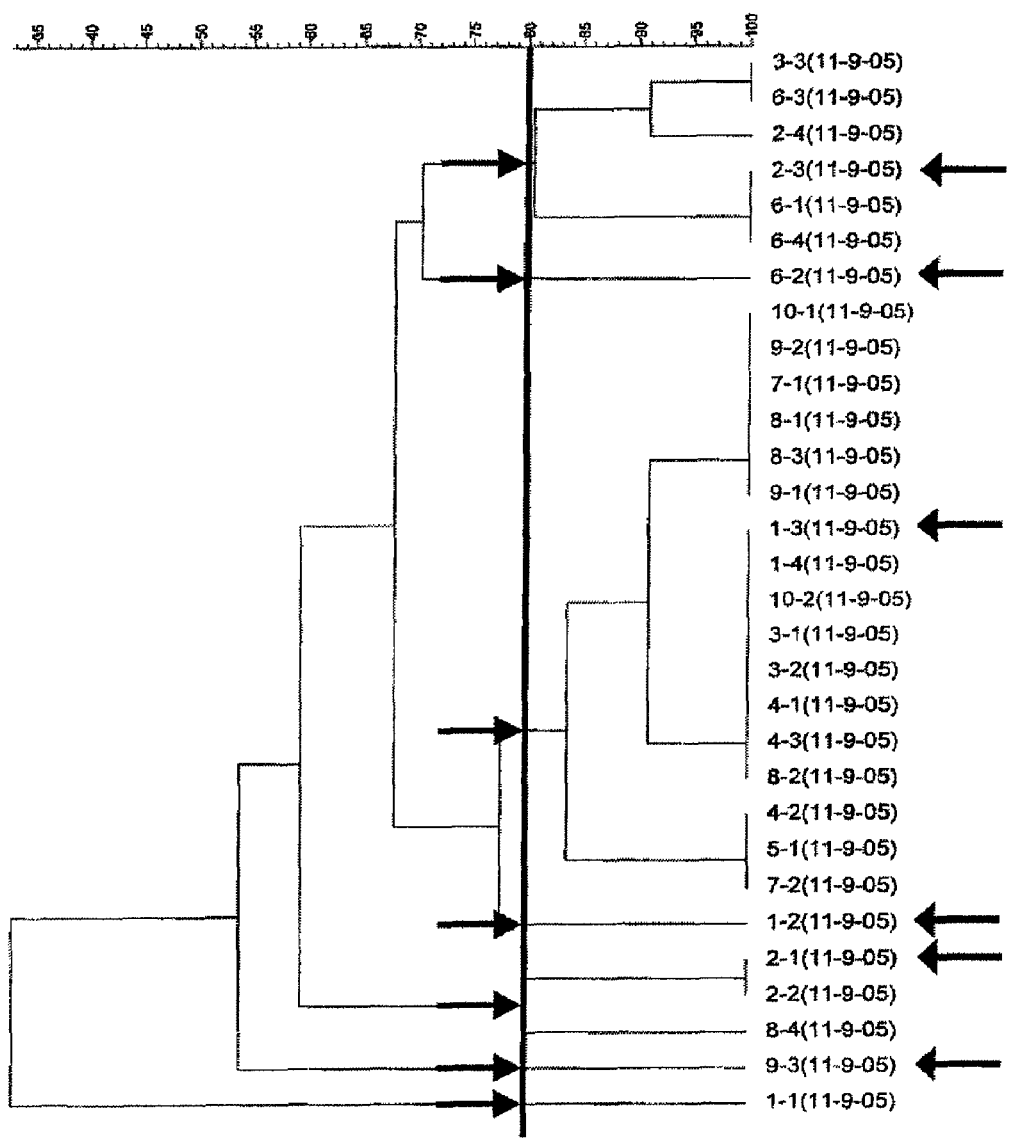

Maxwell, Jr., C. V. et al, "Feeding Weanling Pigs. In: Austin J. Lewis and Lee L. Southern (Ed.)," Swine Nutrition 2nd Edition. (2001) p. 691-717.

McCracken, B. A. et al, "Diet-dependent and diet-independent metabolic responses underlie growth stasis of pigs at weaning," J. Nutr. (1995) 125, 2838-2845.

McDonough, S. P., "Enteric pathogens in intensively reared veal calves," Am. J. Vet. Res. (1994) 55(11):1516-1520.

McMillan, K., "Foal pneumonia: An Illinois survey," An Health and Nutrit 34 (1986).

Morrill, J. L. et al, "Plasma proteins and a probiotic as ingredients in milk replacer," J. Dairy Sci. (1995) 78:902-907.

Mouricout, M. A. et al, "Inhibition of mannose-resistant haemagglutination of sheep erythrocytes by enterotoxigenic *Escherichia coli* in the presence of plasma glycoprotein glycans," FEMS Microbiol. Lett. (1986) 37:145-149.

Muir, L.A. et al, "Prevention of induced lactic acidosis in cattle by thiopeptin," J. Anim. Sci. (1981) 52:635.

Muyzer, G et al, "Profiling of complex microbial populations by denaturing gradient gel electrophoresis analysis of polymerase chain reaction-amplified genes coding for 16S rRNA," Applied and Environmental Microbiology, 59 (3):695-700, Mar. 1993.

Nagy, G et al, "Genetic diversity among *Escherichia coli* isolates carrying f18 genes from pigs with porcine postweaning diarrhea and edema disease," J Clinical Microbiology 37:5:1642-1645, May 1999.

Nagy, G et al, "Genetic diversity among *Escherichia coli* isolates carrying f18 genes from pigs with porcine postweaning diarrhea and edema disease," J Clinical Microbiology 37:5:1642-1645, May 1999.

Niilo, L., "*Clostridium perfringens* in animal disease: a review of current knowledge," Can. Vet. J. (1980) 21:141-148.

Nollet, H. et al, "Protection of just weaned pigs against infection with F18+ *Escherichia coli* by non-immune plasma powder," Vet. Microbiol. (1999) 65:37-45.

Owens, F. N. et al, "Acidosis in cattle: a review," J. Anim. Sci. (1998) 76:275-286.

Parrott, D et al, "Molecular typing of hermolytic *Escherichia coli* isolated from swine," Paper 385 (1 pg), Intl Pig Vet Soc, 2002.

Patterson, J A et al, "Application of prebiotics and probiotics in poultry production," Poultry Science 82:626-631, 2003.

Perez-Bosque, A. et al, "Dietary plasma protein affects the immune response of weaned rats challenged with *S. aureus*," Superantigen B. J. Nutr. (2004) 134:2667-2672.

Power, E. G., "RAPD typing in microbiology—a technical review," J. Hosp. Infect. (1996) 34(4):247-265.

Rehberger, T, "Genome analysis of *Propionibacterium freudenreichii* by pulsed-field gel electrophoresis," Current Microbiology 27(1):Jul. 21-25, 1993 (abstract).

Roche, K. C. et al, "Transforming growth factor beta-1 ameliorates intestinal epithelial barrier disruption by *Cryptosporidium parvum* in the absence of mucosal T lymphocytes," Infect. Immun. (2000) 68:5635-5644.

Roe, S, "Protein purification techniques," 2d Ed. Oxford U. Press, 172-175 (2001).

Slyter, L.L., "Influence of acidosis on rumen function," J. Anim. Sci. (1976) 43:910.

Snoeyenbos, G H, "Protecting chicks and poults from *Salmonellae* by oral administration of "normal" gut microflora," Avian Diseases 22(2):273-287, 1977.

Songer, J. G., "Clostridial enteric diseases of domestic animals," Clinical Microbiology Reviews (1996) 9(2):216-234.

Tam, N. K. M. et al, "The intestinal life cycle of *Bacillus subtilis* and close relatives," J. Bacteriol. (2006) 188:2692-2700.

Tang, M. et al, "Effect of segregated early weaning on postweaning small intestinal development in pigs," J. Anim. Sci. (1999) 77:3191.

Tanner, M. K. et al. "Respiratory and environmental effects of recycled phone book paper versus sawdust as bedding for horses," J Eq Vet Sci (1998) 468-476.

Tannock, G. W., "A special fondness for lactobacilli," Appl. Environ. Microbiol. (2004) 70:3189-3194.

Abe, F et al, "Effect of administration of Bifidobacteria and lactic acid bacteria to newborn calves and piglets," J. Dairy Sci. (1995) 78:2838-2846.

Adami, A. et al, "Piglets fed from birth with the probiotic *Bacillus coagulans* as additive: zootechnical and microbiological aspects," Ann Microbiol Enzimol (1997) 47: 139-149.

Allison, M .J. et al, "Grain overload in cattle and sheep: Changes in microbial populations in the cecum and rumen," Amer. J. Vet Res. (1975) 36:181.

Awad, M M et al, "Synergistic effects of alpha-toxin and perfringolysin O in *Clostridium perfringens*-medicated gas gangrene," Infection & Immunity, 69(12):7904-7910, 2001.

Baker, A. et al, "Development of a *Bacillus subtilis* product for a large commercial swine farm to reduce *Clostridium perfringens* and *Clostridium difficile* in neonatal pigs," J. Anim. Sci. (2007) 85(suppl. 1):102.

Baker, G. C. et al, "Review and re-analysis of domain-specific 16S primers," Journal of Microbiological Methods (2003) 55:541-555.

Barbosa, et al, "Applied and Environmental Microbiology," (Feb. 2005) vol. 71, 2:968-978.

Bembridge et al. "CD45RO expression on bovine T cells: relation to biological function," Immunology, (1995) 86:537-544.

Bertschinger, H U, "*Escherichia coli* infections," Diseases of Swine 8th Ed., Chap. 32, pp. 431-454, 1999.

Bikker, P. et al, "The influence of diet composition and an antimicrobial growth promoter on the growth response of weaned piglets to spray dried animal plasma." Livestock Prod. Sci. (2004) 86:201-208.

Billington et al., "*Clostridium perfringens* Type E animal enteritis isolates with highly conserved, silent enterotoxin gene sequences," Infect. Immun. (1998) 66(9):4531-4536.

Blood, D C, "Diseases caused by bacteria," Veterinary Medicine, 7th Ed., Bailliere, pp. 637-640, 1989.

Bosi, P. et al, "Effect of different spray dried plasmas on growth, ileal digestibility, nutrient deposition, immunity and health of early-weaned pigs challenged with *E. coli* K88," Asian-Aust. J. Anim. Sci. (2001) 14:1138-1143.

Bosi, P. et al, "Spray-dried plasma improves growth performance and reduces inflammatory status of weaned pigs challenged with enterotoxigenic *Escherichia coli* K88," J. Anim. Sci. (2004) 82:1764-1772.

Bosworth, B T et al. "Identification of toxin and pilus genes in porcine *Escherichia coli* using Polymerase Chain Reaction (PCR) with multiple primer pairs," Abstracts of the 97th General Meeting of the Am Society for Microbiology, May 4-8, 1997.

Brosius, J et al, "Complete nucleotide sequence of a 16S ribosomal RNA gene from *Escherichia coli*," Proc Natl Acad Sci USA 75(10:4801-4805, Oct. 1978.

Brown, D. C. et al, "The influence of different management systems and age on intestinal morphology, immune cell numbers and mucin production from goblet cells in post-weaning pigs," Vet. Immunol. Immunopath (2006a) 111:187-198.

Brown, D. C. et al, "Ontogeny of T lymphocytes and intestinal morphological characteristics in neonatal pigs at different ages in the postnatal period," J. Anim. Sci. (2006b) 84:567-578.

Carr, D et al, "Excessive mortality in market-age turkeys associated with cellulitis," Avian Disease 40:736-741, 1996.

Cera, K. R. et al, "Effect of age, weaning and post-weaning diet on small intestinal growth and small intestinal morphology in young swine," J. Anim. Sci. (1988) 66:574.

Coffey, R. et al, "The impact of environment and antimicrobial agents on the growth response of early weaned pigs to spray-dried porcine plasma," J. Anim. Sci. (1995) 73:2532-2539.

Cooper, V, "Diagnosis of neonatal pig diarrhea, "Vet Clinics N Am Food Animal Practice, 16(1):117-161 (2000).

Cromwell, G. L., "Antimicrobial and promicrobial agents. In: A. J. Lewis and L. L. Southern (eds.)," Swine Nutrition. p. 611. CRC Press, Boca Raton, FL (2001).

Cruywagen, C. W. et al, "Effect of *Lactobacillus acidophilus* supplementation of milk replacer on preweaning performance of calves," J. Dairy Sci. (1996) 79:483-486.

Davis. M. E. et al, "Effect of direct-fed microbial and antibiotic supplementation on gastrointestinal microflora, mucin histochemical characterization, and immune populations of weanling pigs," Livestock. Sci. (2007) 108:249-253.

Davis, M.E. et al, "Comparison of direct-fed microbial and antibiotic supplementation on innate and adaptive immune characteristics of weaning pigs," Reprod. Nutr. Dev. (2006) 46(Supp1.1):S63.

Davis, M. E. et al, "Rearing environment affects T lymphocyte populations within the systemic circulation and the gastrointestinal tract of young pigs.," Experimental Biology meeting abstracts [on CD ROM]. (2005) The FASEB Journal, 19, Abstract #43.7.

Davis, M.E. et al. "Dietary supplementation with phosphorylated mannans improves growth response and modulates immune function in weanling pigs," J. Anim. Sci. (2004) 82:1882-1891.

Davis, M. E. et al, "Inhalation Toxicology in the Equine Respiratory Tract," In: Equine Respiratory Diseases, P. Lekeux. International Veterinary Information Service (2002).

Dean-Nystrom, E et al, "Edema disease: a re-emerging problem?," Am Assoc of Swine Veterinarians, pp. 223-224, 2001.

Donald, J, "Treating poultry house floors to improve performance," The Poultry Engineering, Economics & Management Newsletter, Issue No. 23, 4 pgs, May 2003.

Donovan, D. C., "Growth and health of Holstein calves fed milk replacers supplemented with antibiotics or enteroguard," J. Dairy Sci. (2002) 85:947-950.

Dritz, S. et al, "Growth and microbial flora of nonmedicated, segregated, early weaned pigs from a commercial swine operation," JAVMA (1996) 208:711.

Dunlop, R. H., "Pathogenesis of ruminant lactic acidosis," Adv. Vet Sci. Comp Med. (1972) 16:259.

Ecological Laboratories, "Microbe-Lift equine products," EQ1, EQ2 and EQ3 (May 2001) (1 pg).

Elam, C. J. "Acidosis in feedlot cattle: Practical observations," J. Anim. Sci. (1976) 43:898.

Fangman, T. et al, "Segregated early weaning," Swine Health Prod. (1997) 5:195.

Francis, D, "Post-weaning E. coli-diagnosis, treatment, control, and its effect on subsequent growth performance," Am Assoc of Swine Veterinarians, 495-499, 2004.

Fritts, C A et al, "Bacillus subtilis C-3102 (Calsporin) improves live performance and microbioligical status of broiler chickens," Applied Poultry Science, Inc., 9:149-155, 2000.

Fuller, R., "Introduction. In: R. Fuller (Ed.). Probiotics 2: applications and practical aspects," Chapman and Hall, New York. (1997) p. 1.

Gaskins, H. R., "Intestinal bacteria and their influence on swine growth In: Austin J. Lewis and Lee L. Southern (Ed.)," Swine Nutrition 2nd Edition. (2001) p. 585-608.

Gebert, S. et al, "Development of a direct fed microbial to control pathogens associated with turkey poult production," Poult. Sci. (2006) 85(suppl. 1):71.

Gebert, S. et al, "Effect of a Bacillus-based direct-fed microbial on turkey poult performance and changes within the gastrointestinal microflora," J. Anim. Sci. (2007) 85(suppl. 1):249.

Grimes, J L et al, "Heat treatment of turkey litter for reuse as bedding," Int J of Poultry Science 2(5):287-292, 2003.

Hammer, C. et al, "Characterization of a colostrum replacer and a colostrum supplement containing IgG concentrate and growth factors," J. Dairy. Sci. (2004) 87:106-111.

Hatheway, C. L. "Toxigenic Clostridia," Clinical Microbiology Reviews (1990) 3(1):66-98.

Teo et al., "Applied & Environmental Microbiology," (Aug. 2005) vol. 71, 8:4185-4190.

Timmerman, H. M. et al, "Health and growth of veal calves fed milk replacers with or without probiotics," J. Dairy Sci. (2005) 88:2154-2165.

Torrallardona, D. et al, "Effect of fishmeal replacement with spray-dried plasma and colistin on intestinal structure, intestinal microbiology, and performance of weanling pigs challenged with Escherichia coli K99," J. Anim. Sci. (2003) 81:1220-1226.

Van Dijk, A. et al, "Growth performance of weanling pigs fed spray-dried animal plasma: a review," Livestock Production Science (2001a) 68:263-274.

Van Dijk, A. et al, "Growth performance and health status in weanling piglets fed spray-dried porcine plasmas under typical Northern European conditions," J. Anim. Physiol. Anim. Nutr. (Berl). (2002b) 86:17-25.

Vance, H. N., "A survey of the alimentary tract of cattle for Clostridium perfringens," Can. J. Comp. Med. Vet. Sci. (1967) 31:260-264.

Wattiau, P et al, "A PCR test to identify Bacillus subtilis and closely related species and its application to the monitoring of wastewater biotreatment," Appl Microbiol Biotechnol 56:816-819, 2001.

Wattiau et al, Appl. Microbiol Biotechnol 2001, vol. 56, p. 816-819.

Wiard, T et al, "The effect of a biological litter treatment on Salmonella prevalence in turkey breeder flock litter," Poultry Science 80:127 (Suppl. 1):1-4, 2001.

Casey, P. G. et al, "A five-strain probiotic combination reduces pathogen shedding and alleviates disease signs in pigs challenged with Salmonella enterica serovar Typhimurium," Appl. Environ. Microbiol, (2007) 73:1858-1863.

Wiard, T et al, Application of plating enumerations and denaturing gradient gel electrophoresis to study turkey poult gastrointestinal tract bacterial diversity, (4 pgs) presented at the Poultry Science Assoc meeting, Madison, WI 2003.

Wiard, T et al, "Application of plating enumerations and denaturing gradient gel electrophoresis to study turkey poult gastrointestinal tract bacterial diversity," Poster #244 and its abstract, presented at the Poultry Science Assoc meeting, Madison, WI 2003.

Williams, J. G. et al, "DNA polymorphisms amplified by arbitrary primers are useful as genetic markers," Nucleic Acids Res. (1990) 18:6531-6535.

Willoughby, D H et al, "Periodic recurrence of gangrenous dermatitis associated with Clostridium speticum in a broiler chicken operation," J Vet Diagn Invest 8:259-261, 1996.

Wills, "Escherichia coli postweaning diarrhea," Vet Clinics N Am, pp. 138-140, 2000.

Wilson, M, "Segregated early weaning," Pig Lett. (1995) 15:17-20.

Wistuba et al, "Influence of fish oil supplementation on growth and immune system characteristics of cattle," J. Anim. Sci. (2005) 83:1097-1101.

Wu, X. Y. et al, "Characterization of mesophilic bacilli in feces of feedlot cattle," J. Appl. Microbiol. (2007) 102:872-879.

Yang, W., "Effects of direct-fed microbial supplementation on ruminal acidosis, digestibility, and bacterial protein synthesis in continuous culture," Animal Feed Science and Technology, (2004) 114(4): 179-193.

Zhu, X Y, "16S rRNA-based analysis of microbiota from the cecum of broiler chickens," Applied and Environmental Microbiology, 68(1):124-137, Jan. 2002.

Zoetendal, E G et al, Molecular ecological analysis of the gastrointestinal microbiota: a review, J of Nutrition pp. 465-472, 2004.

Clean Air "HM Composter and Odor Eliminator," (1 pg), at least as early as Apr. 16, 2007.

"Copy for immediate release" 'Online! Jan. 13, 2005, pp. 1-2 XP002342562, retrieved from the Internet: URL: http://www.agtechproducts.com/press/DSM_Market_Microsource.pdf>, p. 1, line 1-line 15, p. 2, paragraph 4-last paragraph.

Gyles, C., Workshop #4: Enteric Diseases of Nursery Pigs, pp. 29-41, AASV 32nd Annual Meeting (2001), Nashville, Tenn.

Kim et at. "Aerobic nitrification-denitrification by heterothrophic Bacillus strains". Bioresource Technology. 2005, 96 pages 1897-1906.

NCBI gene bank accession #M59107, Apr. 27, 1993.

NCBI gene bank accession #X73447, Jan. 9, 2004.

"Nonruminant Nutrition: weanling Pigs-additives" Online! 2004, pp. 25-28 XP002342561, Retrieved from the Internet: URL:http//www.fass.org/2004/abstracts/25.PDF> p. 26, col. 2, paragraph 3-5, J. Anim. Sci. vol. 82, Supp. 1/ J. Dairy Sci. vol. 87 Suppl. 1 / Poulty Sci. vol. 83, Supp 1.

Pyne, E et al, Prevalence and genetic diversity of *Clostridum perfringens* isolated from commercial turkey houses, Abstract #432 in Abstracts of papers (2008).

Stable Fresh TM 1:3 concentrate, "An all natural USDA approved concentrate that eliminates stall odors for just pennies per day, per stall," Sterling Creek Enterprises (2 pgs), at least as early as Apr. 16, 2007.
"Watt Feed E-News Feb. 8, 2005" 'Online! Feb. 8, 2005, pp. 1-6, XP002342563, retrieved from the Internet: URL:http://www.wattnet.com/Newsletters/feed/htm/FEBFEED05.htm.
Yang, H. et al, "Effect of adding a bacillus based direct fed microbial on performance of nursery pigs fed diets with or without antibiotics," Abstract # 165. Proc. Midwestern Section ASAS Ann. Meeting 2003: 4 J. Anim. Sci. (2003).
Banach, S et al, "Prevalence, distribution and diversity of pathogenic *E. coli* in commercial turkey poult production," Presented at the Poultry Science Association Annual Meeting, Madison, WI, Jul. 2003.

* cited by examiner

METHODS OF TREATING PIGS WITH *BACILLUS* STRAINS

CROSS-REFERENCE TO RELATED APPLICATIONS

This application claims priority under 35 U.S.C. §119(e) to U.S. Provisional Patent Application No. 61/036,741, filed Mar. 14, 2008, the entirety of which is incorporated by reference herein.

FIELD DESCRIBED HEREIN

The invention relates to controlling disease in pigs, enhancing pig performance, and improving the health of pigs with *Bacillus* strains.

DESCRIPTION OF THE RELATED ART

Enteric clostridial infections in swine occur predominantly in the neonatal period but are also associated with hemorrhagic bowel syndrome affecting pigs in the finishing period. Although immunization against *C. perfringens* type C has greatly reduced pre-weaning mortality, no commercial vaccines are currently available for *C. perfringens* type A or *C. difficile*. *C. perfringens* type A and *C. difficile* infections are now recognized with increasing frequency in neonatal pigs and approaches to diagnosis and prophylaxis are both different and more complex than those for type C infections.

There is a lack of efficacious commercial vaccines for *C. perfringens* type A and *C. difficile*. Conventional control strategies for these clostridial enteric disease include fecal feedback programs, antibiotics, oregano oil, and probiotics. Unfortunately, the efficacy of these therapies has been limited.

Feeding antibiotics such as bacitracin to pigs has many drawbacks to feeding antibiotics to livestock, including consumer acceptance. There is also concern about selection of antibiotic-resistant bacteria. Antibiotics are also expensive and have variable effectiveness. In addition, some countries have banned the feeding of antibiotics to animals. For example, on Jan. 1, 2006, the European Union banned the feeding of all antibiotics and related drugs to livestock for growth promotion purposes. The sweeping new policy follows up a 1998 ban on the feeding of antibiotics that are valuable in human medicine to livestock for growth promotion. Now, no antibiotics can be used in European livestock for growth promotion purposes.

Oregano oil has also been used to combat clostridial disease in pigs and improve health of swine. Etheric oils from oregano exert antibacterial effects. However, the use of phytogenic feed additives is controversial, and the efficacy of this therapy has been limited.

Pigs and piglets suffer from scours, that is, diarrhea, which can be caused by bacteria such as *Escherichia colibacillosis* (*E. coli*) and *Clostridium perfringens* Types A and C. Scours can cause death losses and severe production losses, including weight loss, if left untreated.

In view of the foregoing, it would be desirable to provide methods of using one or more *Bacillus* strains to treat or prevent *Clostridium*-based disease in pigs and to enhance performance of pigs.

SUMMARY OF THE INVENTION

The invention, which is defined by the claims set out at the end of this disclosure, is intended to solve at least some of the problems noted above. Methods are provided. In one embodiment of the method, an effective amount of at least two *Bacillus* strains is administered to a pig. The *Bacillus* strains are selected from strains 22CP1 (ATCC PTA-6508), 3AP4 (ATCC PTA-6506), 15AP4 (ATCC PTA-6507), 2084 (NRRL B-50013), LSSAO1 (NRRL B-50104), and 27 (NRRL B-50105).

In another embodiment of the method, an effective amount of *Bacillus* strains 3AP4 (ATCC PTA-6506) and LSSAO1 (NRRL B-50104) is administered to a pig. The pig can be a gestating pig, a lactating pig, or any other pig.

BRIEF DESCRIPTION OF THE DRAWINGS

Preferred exemplary embodiments described herein are illustrated in the accompanying drawings, in which like reference numerals represent like parts throughout and in which:

FIG. 1 is the dendrogram representing the genetic relatedness among 30 isolates of *C. perfringens* recovered from a first set of swabs.

FIG. 2 is the dendrogram representing the genetic relatedness among *C. perfringens* isolates harvested from a second set of swabs.

FIG. 3 is the dendrogram representing the genetic relatedness among 40 isolates of *C. perfringens* recovered from a third set of swabs.

FIG. 4 is a graph showing clostridia counts (CFU/g of tissue) from the ileum and distal colon of pigs from control and DFM supplemented sows (section×treatment interaction: P=0.14, SE=$5.5\times10^5$; a, b Means without a common letter differ, P>0.05).

Before explaining embodiments described herein in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

As used herein, "performance" refers to the growth of an animal, such as a pig, measured by one or more of the following parameters: average daily gain (ADG), weight, scours, mortality, feed conversion, which includes both feed:gain and gain:feed, and feed intake. "An improvement in performance" or "improved performance" as used herein, means an improvement in at least one of the parameters listed under the performance definition.

The present application provides methods of administering an effective amount of one or more *Bacillus* strains to a pig. In one embodiment, the methods improve performance of pigs. Thus, it may be economical for a swine producer to routinely administer one or more *Bacillus* strain, either individually or in combination with other *Bacillus* strains, not only to treat and prevent disease, but also to improve performance.

In another embodiment administration of one or more *Bacillus* strains inhibit pathogenic *Clostridium*, such as *C. perfringens* and *C. difficile* in pigs. The methods may also be used to reduce or even prevent clostridial disease in pigs not currently infected with clostridial pathogens.

In at least some embodiments of the method, feeding one or more *Bacillus* strain to pigs also include the following: a decrease in percent of scouring litters of pigs, improved 15 d piglet body weight, improved piglet average daily gain (ADG), and decrease in sow weight loss.

Methods of administering one or more *Bacillus* strain to a piglet are also provided. Such methods may include feeding the one or more *Bacillus* strain to a mother of a piglet. The strain(s) may be fed during gestation, lactation, or both. The one or more *Bacillus* strain may also be fed to nursery pigs and to grow-finish pigs.

*Bacillus* Strains:

*Bacillus* strains have many qualities that make them useful for compositions that are ingested by animals. For example, *Bacillus* strains produce extracellular enzymes, such as proteases, amylases, and cellulase. In addition, *Bacillus* strains produce antimicrobial factors, such as gramicidin, subtilin, bacitracin, and polymyxin. *Bacillus* strains are also spore formers and thus, are stable. Additionally, several species of *Bacillus* have GRAS status, i.e., they are generally recognized as safe. All *B. subtilis* strains are GRAS. The *Bacillus* strains described herein are aerobic and facultative sporeformers. *Bacillus* species are the only sporeformers that are considered GRAS. Feeding microorganisms that have GRAS status to livestock is an acceptable practice amongst producers, veterinarians, and others in the livestock industry.

*Bacillus* strains that can be used in the methods described herein include the following *B. subtilis* strains: 22CP1, 3AP4, 15AP4, 2084, LSSAO1, and 27. Other *Bacillus* strains are included within the scope described herein. On Jan. 12, 2005, strains 22CP1, 3AP4, and 15AP4 were deposited at the American Type Culture Collection (ATCC), 10801 University Blvd., Manassas, Va. 20110-2209 and given accession numbers PTA-6508, PTA-6506 and PTA-6507, respectively. Strains 2084, LSSAO1, and 27 were deposited on Mar. 8, 2007, Jan. 22, 2008, and Jan. 24, 2008, respectively, at the Agricultural Research Service Culture Collection (NRRL), 1815 North University Street, Peoria, Ill., 61604 and given accession numbers NRRL B-50013, NRRL B-50104, and NRRL B-50105, respectively. All deposits were made under the provisions of the Budapest Treaty on the International Recognition of the Deposit of Microorganisms for the Purposes of Patent Procedure.

*Bacillus* strains 22CP1, 3AP4 and 15AP4 were isolated from different geographical regions of North America and from different environmental sources. Specifically, strain 22C-P1 was isolated from a swine lagoon from the eastern United States, strain 3AP4 was isolated from chicken litter from Canada, and strain 15AP4 was isolated from turkey litter from the Western United States.

*Bacillus* strains described herein can be combined, such as in the non-limiting examples of combinations of *Bacillus* strains shown in Table 1 below and then fed to pigs. A combination can be determined based on the *Clostridium* strains present in a specific production facility or other environment. The combination of *Bacillus* strains can be modified if the *Clostridium* strains change. In addition, because the strains are also useful in asymptomatic animals, the combination of *Bacillus* strains that are fed can be independent of the *Clostridium* strains present in a specific production facility or other environment.

TABLE 1

| Formula | Strains | Counts and Application Rates |
| --- | --- | --- |
| 25%, 25%, 25%, 25% | 3AP4, 2084, 27, LSSAO1 | 7.5 × 10$^8$ CFU/g of product<br>Gestation-1 lb of product per ton of feed<br>Lactation-5.0 lb of product per ton of feed |
| 25%, 25%, 25%, 25% | 3AP4, 15AP4, 27, LSSAO1 | 1.5 × 10$^8$ CFU/g of product<br>Gestation-1 lb of product per ton of feed<br>Lactation-5.0 lb of product per ton of feed |
| 50%, 50% | LSSAO1, 3AP4 | 7.5 × 10$^8$ CFU/g of product<br>Gestation-1 lb of product per ton of feed<br>Lactation-5.0 lb of product per ton of feed |

Although not intended to be a limitation to the present disclosure, it is believed that inhibition of *Clostridium* pathogens is accomplished by the *Bacillus* strain(s) via the secretion of an active metabolite from the *Bacillus*.

Preparation of the *Bacillus* Strains:

The *Bacillus* strains are grown in a liquid nutrient broth, preferably to a level at The counts may be increased or decreased from this number and still have complete efficacy. CFU or colony forming unit is the viable cell count of a sample resulting from standard microbiological plating methods. The term is derived from the fact that a single cell when plated on appropriate medium will grow and become a viable colony in the agar medium. Since multiple cells may give rise to one visible colony, the term colony forming unit is a more useful unit measurement than cell number.

The *Bacillus* strains of the present invention are produced by fermentation of the bacterial strains. Fermentation is started by scaling-up a seed culture. In one embodiment, *Bacillus* cultures are grown in growth medium, such as TSB or TSA, for 24 to 48 hrs at 32° C. with agitation in a shaking incubator to a final pH of 7.3±0.2. This involves repeatedly and aseptically transferring the culture to a larger and larger volume to serve as the inoculum for the fermentation, which is carried out in large stainless steel fermentors in medium containing proteins, carbohydrates, and minerals necessary for optimal growth. A non-limiting exemplary medium is TSB. After the inoculum is added to the fermentation vessel, the temperature and agitation are controlled to allow maximum growth. Once the culture reaches a maximum population density, the culture is harvested by separating the cells from the fermentation medium. This is commonly done by centrifugation.

The count of the culture can then be determined and is important when combined with a carrier. At the time of manufacture, the *Bacillus* count preferably is at least about 1.0× 10$^{11}$ CFU/g.

Use of the *Bacillus* Strains:

The *Bacillus* strains described herein can be used in direct-fed microbials, that is they can be fed directly to swine. In one embodiment, one or more *Bacillus* strains is fed to female pig breeding stock during gestation and/or during lactation When one or more *Bacillus* strains are fed to female pig breeding stock, the strain(s) is transferred to piglets at least through the oral-fecal route. In another embodiment, piglets can be fed one or more *Bacillus* strains from the day of birth to weaning at about 17-24 days old. This can be done with an oral drench or any other suitable form of delivering the *Bacillus* strains. In other embodiments, nursery pigs are fed one or more *Bacillus* strains. The strains can also be fed to grow/finish pigs and to pigs of different ages.

Administration of one or more *Bacillus* strains to animals is accomplished by any convenient method, including adding the *Bacillus* strains to the animals' drinking water, to their feed, or to the bedding, or by direct oral insertion, such as by an aerosol. *Bacillus* strains preferably are administered as spores.

*Bacillus* strains described herein may be presented in various forms, for example as a top dress, liquid drench, gelatin capsule, or gels. In one embodiment of the top dress form, freeze-dried *Bacillus* fermentation product is added to a carrier, such as whey, maltodextrin, sucrose, dextrose, limestone (calcium carbonate), rice hulls, yeast culture, dried starch, sodium silico aluminate. In one embodiment of the liquid drench, freeze-dried *Bacillus* fermentation product is added to a carrier, such as whey, maltodextrin, sucrose, dextrose, dried starch, sodium silico aluminate, and a liquid is added to form the drench. In one embodiment of the gelatin capsule form, freeze-dried *Bacillus* fermentation product is added to a carrier, such as whey, maltodextrin, sugar, limestone (calcium carbonate), rice hulls, yeast culture dried starch, and/or sodium silico aluminate. The *Bacillus* and carrier are enclosed in a degradable gelatin capsule. In a one embodiment of the gels form, freeze-dried *Bacillus* fermentation product is added to a carrier, such as vegetable oil, sucrose, silicon dioxide, polysorbate 80, propylene glycol, butylated hydroxyanisole, citric acid, and artificial coloring to form the gel. In all of the examples, multiple carriers can be used.

To prepare direct-fed microbials, the cultures and the carrier can be added to a ribbon or paddle mixer and mixed preferably for about 15 minutes, although the timing can be increased or decreased. The components are blended such that a uniform mixture of the carrier and cultures result. The final product is preferably a dry, flowable powder.

The following dosages are for all of the *Bacillus* strains that are fed. That is, if a single strain is fed, then that single strain is used at the listed dosage. If multiple strains are used, substantially equal amounts of each strain are used for a total dosage that is listed. For example, where two strains are used, half of each is used to arrive at the total dosage.

When fed to female pig breeding stock during gestation, the one or more *Bacillus* strains with a total microbial count of $7.5 \times 10^8$ CFU/g of DFM including one or more strain blended to this count in a carrier is fed at a rate of 1 lb of the DFM per ton of feed, to provide $3.75 \times 10^5$ CFU/g of feed. When fed during lactation, the one or more *Bacillus* strains with a total microbial count of $7.5 \times 10^8$ CFU/g of product is fed at a rate of 5 lbs of the DFM per ton of feed, to provide $8.5 \times 10^8$ CFU/g of feed. In one embodiment, the DFM is top dressed onto feed. In another embodiment, the DFM is blended into the complete feed. The DFM can be administered in other ways known in the art, at other dosages, and at other stages in the pig's life.

In at least one embodiment of the liquid drench and gel, each has about $1 \times 10^4$ to about $1 \times 10^{10}$ CFU/day. In another embodiment of the liquid drench and gel, each has about $1 \times 10^8$ CFU/day. In at least one embodiment of the top dress, basemix, and premix, each includes about. $7.5 \times 10^8$ CPU/g of top dress, basemix, or premix. This can be added to feed at 1 lb/ton of feed, resulting in $3.75 \times 10^5$ CFU/g of feed. However, other dosages can also be used. In one embodiment of a dosage for inclusion into water, about $1 \times 10^3$ CFU/animal/day to about $1 \times 10^{10}$ CFU/animal/day is used. Some embodiments of a dosage for inclusion into water use about $1 \times 10^8$ CFU/animal/day. While these examples use freeze-dried *Bacillus*, it is not necessary to freeze-dry the *Bacillus* before feeding it to animals. For example, spray-dried, fluidized bed dried, or solid state fermentation *Bacillus* or *Bacillus* in other states may be used. The strains can also be administered in a wet cell slurry paste, with or without preservatives, in concentrated, unconcentrated, or diluted form.

EXAMPLES

The following Examples are provided for illustrative purposes only. The Examples are included herein solely to aid in a more complete understanding of the presently described invention. The Examples do not limit the scope described herein described or claimed herein in any fashion.

Example 1

An initial pool of *Bacillus* strains were obtained from various environmental samples and a library of *Bacillus* strains. *Bacillus* strains were selected that inhibit representative members from the clusters of *Clostridium*. For this, tubes were seeded, each with a representative pathogen from a representative cluster. Supernatant from a *Bacillus* strain was added to the seeded tubes and incubated. After incubation, the optical density (OD) of control and *Bacillus* supernatant treated tubes was measured for each pathogen. Colonies of *Bacillus* that produced a lowered OD were then picked, and the *Bacillus* isolates were grown.

*Clostridium* samples were obtained and screened as follows. *Clostridium* samples were obtained from swabs taken from farrowing units. The swabs were taken from piglets, sows, and the environment. The samples were plated for *Clostridium*, and colonies were isolated. DNA was isolated from the colonies, and multiplex PCR was performed of the α-toxin gene of *Clostridium* was used to identify pathogens. To understand the diversity of the *Clostridium* pathogens, a comparison of the isolates was performed using RAPD-PCR. From the RAPD-PCR results, in a dendogram, clusters of *Clostridium* were identified.

Useful *Bacillus* strains were selected by identifying representative *Clostridium* pathogens present in swine production facilities, such as farrowing units. In general, once *Clostridium* pathogens were identified, *Bacillus* strains were screened to determine which of them inhibit growth of the identified pathogens. *Bacillus* strains that were useful against both *C. perfringens* and *C. difficile* were identified. Specifically, the *Bacillus* strains were selected and tested as is described below.

A total of 30 presumptive *C. perfringens* isolates were obtained from the nine rectal swabs. The results of multiplex PCR identified all 30 of the isolates as *C. perfringens* type A. Twenty-two of the isolates also contained the recently identified β2-toxin which has been correlated with GI disease in domestic animals. RAPD PCR was performed on the pathogenic isolates to determine the relatedness among the strains. The results were then analyzed to construct a dendrogram (shown in FIG. 1), which was used to select isolates for bacteriocin screening. Isolates connected to the same branch on the right of the vertical line, drawn at 80% similarity, were considered to be members of the same family. Seven families were observed and are marked with arrows on the left. The arrows on the right signify which isolates were screened against *Bacillus* strains described herein.

The *Bacillus* strains listed in Table 2 highly significantly (>90%) inhibited the growth of all six *C. perfringens* isolates. These six *C. perfringens* isolates represent 96.7% of the total diversity observed. Table 2 below includes the results of screening performed on six *C. perfringens* isolates representative of unique families isolated from the swabs. One family containing only isolate 1-1, which failed to grow for the assay, was not tested. All six families tested were significantly inhibited (>50%) by the *Bacillus* strains listed in Table 2.

TABLE 2

Isolates from swabs
% Inhibition

| C. perfringens Type A strain | Bacillus strains | | | | | |
|---|---|---|---|---|---|---|
| | 22CP1 | 15A-P4 | 3AP4 | BS2084 | 27 | LSSA01 |
| 1-2 | 98.2 | 100 | 99.1 | 100 | 100 | 97.3 |
| 1-3 | 99.2 | 99.2 | 97.7 | 96.2 | 100 | 99.2 |
| 2-1 | 100 | 96.8 | 98.9 | 98.9 | 100 | 100 |
| 2-3 | 91.7 | 98.1 | 98.1 | 98.1 | 99.1 | 98.1 |

TABLE 2-continued

Isolates from swabs
% Inhibition

| C. perfringens Type A strain | Bacillus strains | | | | | |
|---|---|---|---|---|---|---|
| | 22CP1 | 15A-P4 | 3AP4 | BS2084 | 27 | LSSA01 |
| 6-2 | 97.7 | 97.7 | 94.6 | 98.5 | 98.5 | 97.7 |
| 9-3 | 95.9 | 95.1 | 96.7 | 95.9 | 95.9 | 96.7 |

Example 2

Clostridium samples were obtained and screened as is described above in Example 1. The Bacillus strains were selected and tested as is described in this example.

Figure 2:
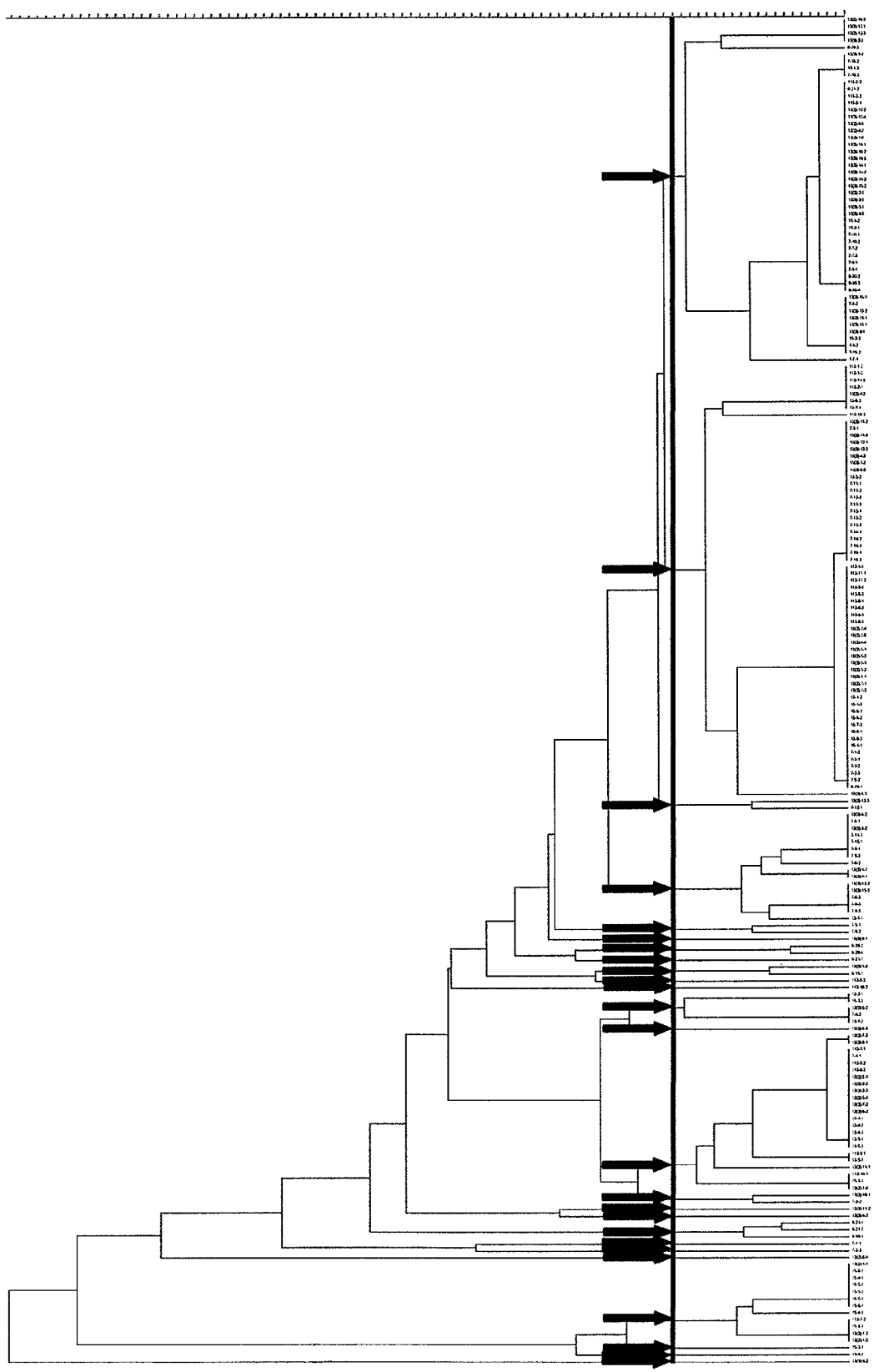

A total of 194 C. perfringens isolates were obtained from six sets of swab samples. The results of multiplex PCR identified 189 of the isolates as C. perfringens type A, four isolates as C. perfringens type E, and one as C. perfringens type C. RAPD PCR was performed on the pathogenic isolates to determine the relatedness among the strains. The results were then used to construct a dendrogram (shown in FIG. 2), which was used to identify unique families for screening of Bacillus strains. Isolates connected to the same branch on the right of the vertical line, drawn at 80% similarity, were considered to be members of the same family. Each of these families is indicated by an arrow.

Twenty-one representative isolates were chosen for bacteriocin screening against the strains of Bacillus shown in Table 3. The growth of all but two C. perfringens isolates was significantly (>50%) inhibited by a combination of the six Bacillus strains. More bacteriocin screening will be performed to cover all unique families observed to date.

Table 3 below includes the results of bacteriocin screening performed on 21 representative isolates of 21 unique families of C. perfringens. All but two of the isolates were significantly inhibited (>50%) by the six Bacillus strains shown in Table 3.

TABLE 3

Isolates from swabs
% Inhibition

| Clostridium strain | Identity of C. perfringens | Bacillus strains | | | | | |
|---|---|---|---|---|---|---|---|
| | | 22CP1 | 15A-P4 | 3AP4 | BS2084 | 27 | LSSA01 |
| 21-1 | Type A | 31.1 | 37.8 | 60 | 5.6 | 0 | 22.2 |
| 28-2 | Type A | 0 | 0 | 0 | 9.7 | 0 | 3.2 |
| 31-1 | Type A | 17.3 | 14.7 | 9.3 | 6.7 | 6.7 | 0 |
| 2-2 | Type A | 98.3 | 100 | 33.3 | 98.3 | 99.2 | 99.2 |
| 5-3 | Type A | 98.5 | 98.5 | 97.7 | 100 | 99.2 | 99.2 |
| 10-2 | Type A | 98.3 | 99.2 | 37.5 | 99.2 | 100 | 98.3 |
| 3-2 | Type A | 98.9 | 98.9 | 57.9 | 100 | 98.9 | 98.9 |
| 4-2 | Type A | 99.1 | 100 | 86.4 | 100 | 99.1 | 99.1 |
| 6-2 | Type A | 99.2 | 99.2 | 62.5 | 99.2 | 99.2 | 99.2 |
| 2-3 | Type A | 96.9 | 97.7 | 96.2 | 98.5 | 97.7 | 97.7 |
| 5-2 | Type A | 97.3 | 89.1 | 96.4 | 98.2 | 99.1 | 98.2 |
| 8-3 | Type A | 99.1 | 98.2 | 98.2 | 99.1 | 98.2 | 97.3 |
| 8-4 | Type A | 96.2 | 91.5 | 97.2 | 99.1 | 97.2 | 98.1 |
| 10-1 | Type A | 98.4 | 98.4 | 98.4 | 96.8 | 96.8 | 96 |
| 11-2 | Type E | 97.7 | 98.5 | 98.5 | 98.5 | 98.5 | 98.5 |
| 7-1-1 | Type E | 94.5 | 96.4 | 96.4 | 96.4 | 95.5 | 95.5 |
| 7-3-3 | Type E | 42.3 | 41.5 | 50.8 | 75 | 42.3 | 73.8 |
| 7-4-1 | Type A | 97.7 | 98.5 | 96.9 | 98.5 | 98.5 | 97.7 |
| 13-1-2 | Type A | 97.5 | 96.7 | 95.8 | 99.2 | 98.3 | 96.7 |
| 13-4-2 | Type C | 5.9 | 17.6 | 0 | 31.8 | 0 | 77.6 |
| 13-9-1 | Type A | 99.1 | 99.1 | 98.2 | 99.1 | 99.1 | 99.1 |

Isolates in the first three rows were not subjected to heat treatment, and are likely contaminated which explains their abnormal resistance to the Bacillus strains of Table 3. All other swabs from which Clostridium strains shown in Table 3 were obtained were heat treated to kill any non-spore forming contaminants.

Example 3

Clostridium samples were obtained and screened as is described above in Examples 1 and 2. The Bacillus strains were selected and tested as is described in this example.

Figure 3:
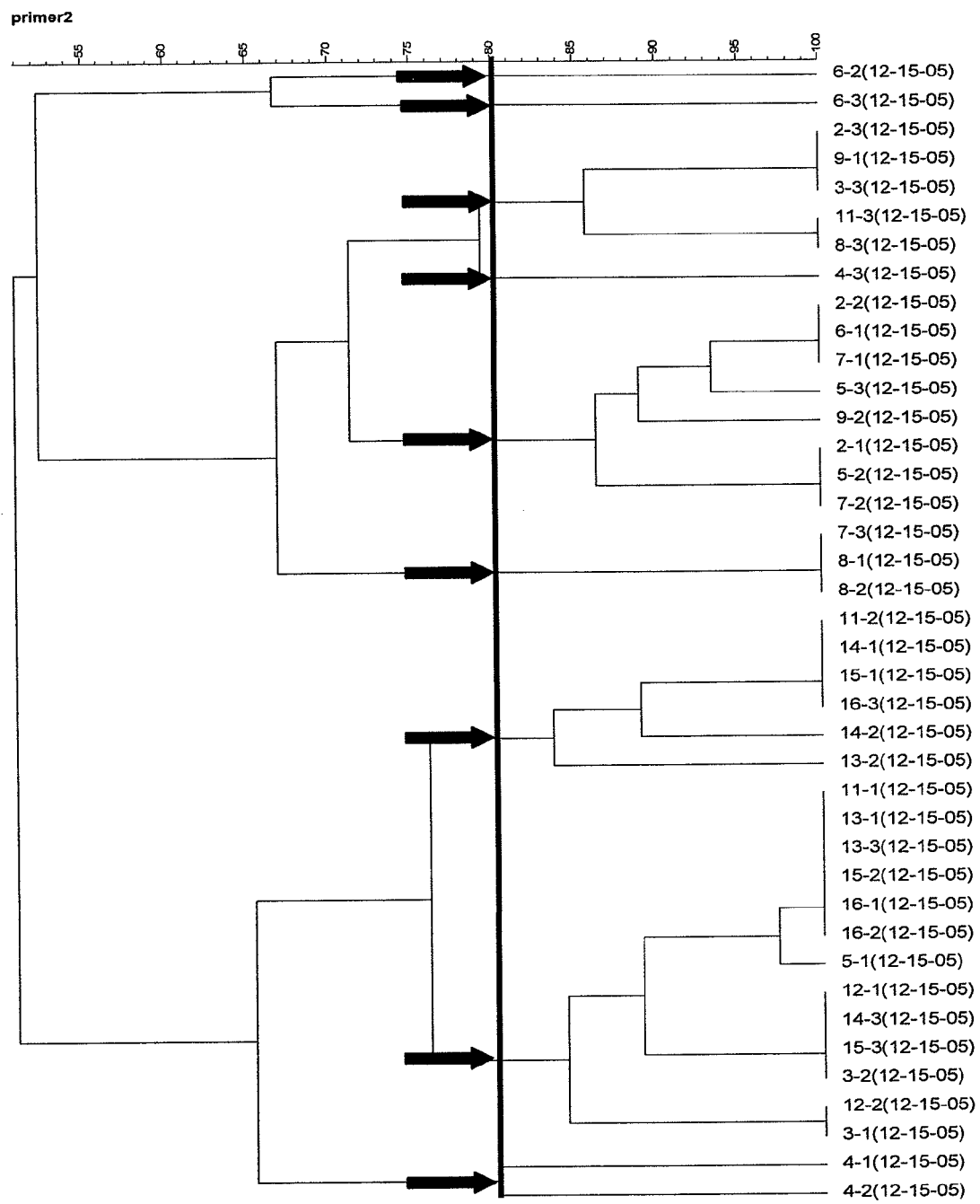

A total of 40 presumptive C. perfringens isolates were obtained, using Perfringens Agar selective media, from sixteen rectal swabs. The results of multiplex PCR identified all 40 of the isolates as C. perfringens type A. Thirty-five of the isolates also contained the recently identified β2-toxin which has been correlated with GI disease in domestic animals. RAPD PCR was performed on the pathogenic isolates to determine the relatedness among the strains. The results were then analyzed to construct a dendrogram (shown in FIG. 3), which was used to select isolates for bacteriocin screening. Isolates connected to the same branch on the right of the vertical line, drawn at 80% similarity, were considered to be members of the same family. Nine families were observed and are marked with arrows. The representative isolates screened against the Bacillus are listed in Table 4.

Nine representative isolates were chosen for screening against bacteriocins produced by the strains of *Bacillus* listed in Table 4. The growth of all nine isolates was highly significantly (>90%) inhibited, and represent 100% of the diversity observed to date. These results suggest that a *Bacillus* direct fed microbial including these strains will be effective for the control of *C. perfringens* in this system.

Table 4 below includes the results of bacteriocin screening performed on nine *C. perfringens* isolates representative of unique families isolated from the swab samples. All nine families tested were significantly inhibited (>50%) by the *Bacillus* shown in Table 4. These nine families cover all of the diversity observed within this sample set.

TABLE 4

| *Clostridium* isolates from swabs % Inhibition | | | |
|---|---|---|---|
| *Clostridium* | Identity of | *Bacillus* strains | |
| strain | *C. perfringens* | 3AP4 | 27 |
| 2-2 | Type A | 97.1 | 88.9 |
| 2-3 | Type A | 100 | 100 |
| 4-1 | Type A | 94.5 | 97.3 |
| 4-3 | Type A | 94.7 | 96.8 |
| 6-2 | Type A | 95 | 97.5 |
| 6-3 | Type A | 98.9 | 95.8 |
| 7-3 | Type A | 100 | 100 |
| 11-1 | Type A | 97.8 | 100 |
| 11-2 | Type A | 100 | 100 |

Example 4

This example describes piglet performance trials and demonstrates improvements in scour scores and decreased percent scouring litters with the administration of *Bacillus* strains 3AP4 and LSSA01. The strains were administered as a dried *B. subtilis* fermentation product developed. These strains were specifically formulated to be effective against clostridial disease in neonatal pigs. This study was run to determine if these strains may also provide a performance benefit by decreasing the load of pathogenic clostridia in a subclinical herd and to determine the efficacy of these strains for enhancing sow and piglet performance during lactation in a commercial sow unit. This research evaluated the performance enhancing benefits of feeding these strains to sows whose piglets were known to be infected with *Clostridium perfringens* type A.

Materials and Methods:

A total of 121 sows (Genetiporc) and their respective litters were evaluated in a commercial swine production facility. At day 72 of gestation (last 6 weeks of gestation), sows were allotted to three treatments by parity group (1 vs. 2+) and 114 day farrowing date. Blocks consisted of three sows of the same parity group. Three treatments were administered to the sows during gestation and lactation: 1) a negative control (n=44) diet devoid of BMD and *Bacillus* strains 3AP4 and LSSA01, 2) a positive control diet as 1) supplemented with BMD (n=39), and 3) as 1) with *Bacillus* strains 3AP4 and LSSA01 supplementation (n=38). Feed-grade antibiotics (i.e. CTC, Pulmotil, etc.) were not used in the gestation and lactation feeds during the trial period. Experimental treatments were top-dressed one time daily to approximate 250 g/ton BMD and 454 g/ton *Bacillus* strains 3AP4 and LSSA01. The *Bacillus* strains 3AP4 and LSSA01 top-dress was formulated by combining 10 lb of *Bacillus* strains 3AP4 and LSSA01 ($7.5\times10^8$ cfu/g product) and 5 lb of cornstarch to provide the equivalent of 1 lb/ton when 1 teaspoon/day was top-dressed, which provided $2.25\times10^9$ cfu/day. BMD was top-dressed beginning two weeks prior to lactation until weaning, whereas *Bacillus* strains 3AP4 and LSSA01 was top-dressed beginning six weeks prior to lactation until weaning.

Sows were weighed prior to farrowing and at weaning to determine sow body weight change over the course of the lactation period. Litters were cross-fostered within treatment groups only and to a minimum of 9-10 pigs/litter within the first 24 hours post-farrowing. Litter weights were determined after standardization and at weaning to calculate piglet average daily gain (ADG). Scouring litters were recorded to determine the percentage of litters scouring for each treatment, and scouring severity was determined for each litter daily based on subjective visual evaluation using a 0 to 3 scale (0=no scours and 3=heavy scours).

Data were analyzed using the PROC MIXED procedure of SAS with litter considered the experimental unit with the exception of percentage of scouring litters and scour severity scores which was analyzed by the Kruskal-Wallis nonparametric test.

Results and Discussion:

Treatments impacted (P=0.008) the percentage of scouring litters, such that litters born to sows supplemented with *Bacillus* strains 3AP4 and LSSA01 or BMD had a lower percentage of scouring litters than negative control sows (Table 5). Furthermore, *Bacillus* strains 3AP4 and LSSA01 supplementation tended to result in a lower (P=0.08) percentage of scouring litters than treatment with BMD. Treatments affected (P=0.01) severity of scours as indicated by litter scour scores, such that sows provided *Bacillus* strains 3AP4 and LSSA01 had the lowest scour severity score of the three treatments. Furthermore, scour severity tended to be less (P=0.06) in litters born to sows provided *Bacillus* strains 3AP4 and LSSA01 compared to sows supplemented with BMD.

Conclusions:

These data indicate that BMD and *Bacillus* strains 3AP4 and LSSA01 are effective in controlling neonatal piglet scours. In addition, *Bacillus* strains 3AP4 and LSSA01 may provide additional benefit over BMD by decreasing the severity of scouring events.

TABLE 5

| Sow and piglet effects of *Bacillus* strains 3AP4 and LSSA01 or BMD supplementation to gestating sows prior to farrowing. | | | | | |
|---|---|---|---|---|---|
| | | Parity, | Litter | Piglet scours | |
| Treatment | n | n | size, n[1] | Severity[3] | %[4] |
| *Bacillus* strains 3AP4 and LSSA01 (6-wk) | 38 | 3.66 | 11.5 | 0.11 | 10.5 |
| BMD (2-wk) | 39 | 4.03 | 11.1 | 0.41 | 25.6 |
| Negative control (NC) | 44 | 3.86 | 10.9 | 0.57 | 40.9 |
| Pooled standard error of the mean (SEM) | | 0.36 | 0.2 | — | — |
| Significance[2] | | | | | |
| Treatment | | 0.779 | 0.139 | 0.011 | 0.008 |
| *Bacillus* strains 3AP4 and LSSA01 & BMD vs NC | | 0.960 | 0.159 | — | — |
| *Bacillus* strains 3AP4 and LSSA01 vs BMD | | 0.481 | 0.156 | 0.064[5] | 0.088[5] |

[1]Litter size reflects the average number of pigs/litter following standardization.
[2]Levels of significance (P-values) accorded to the main effect of treatment and a single degree-of-freedom comparison of *Bacillus* strains 3AP4 and LSSA01 and BMD supplementation.
[3]Severity (0 = no scours, 3 = heavy scours) of scouring of pigs in a litter was analyzed by the Kruskal-Wallis nonparametric test.
[4]Percentage of litters exhibiting signs of scouring was analyzed by the Kruskal-Wallis nonparametric test.
[5]*Bacillus* strains 3AP4 and LSSA01 and BMD treatment data (excluding negative control data) analyzed by the Kruskal-Wallis nonparametric test.

Example 5

This example describes research conducted to document that *Bacillus subtilis* organisms fed to sows during gestation and lactation were transferred to suckling piglets. Specifically, this research identified the fecal-oral transfer of *Bacillus* spores from *Bacillus* strains 3AP4 and LSSA01 into the nursing piglets from supplemented sows. However, other *Bacillus* sporeformers are believed to also would be transferred via the fecal-oral route. This research also evaluated the effectiveness of these spores isolated from sow and piglet feces against *Clostridium perfringens*.

This example documented the presence of *Bacillus* spores from supplemented sows in their feces and any transfer to their piglets via the fecal-oral route of transmission. This example also measured the inhibition of *Clostridia* by *Bacillus* organisms isolated from sow and piglet feces from control- and fed sows fed strains 3AP4 and LSSA01.

Materials and Methods:

Two treatments were used: 1) control and 2) strains 3AP4 and LSSA01 supplemented to the sow 2 weeks prior to and throughout lactation. Gestation and lactation diets that comprised typical farm management rations but without feed-grade antibiotics or microbial products were used as the control basal diets in this experiment. The strains 3AP4 and LSSA01 treatment was top-dressed over the gestation ration administered to each sow and was mixed, bagged and administered to treated sows during the lactation phase. The strains were formulated to provide 3.75 CFU/g of feed with each method of application. Nine sows were randomly assigned to the control treatment and 27 sows represented the treatment with strains 3AP4 and LSSA01. Fecal samples (~100 g) were collected from 5 control sows and 15 treated sows before supplementation with strains 3AP4 and LSSA01, on d −1 prior to farrowing (d 0), and d 14 after farrowing. Samples were also collected from piglets from each sows litter on d 3, 5, and 14 after farrowing. Fecal samples obtained from the pigs within the same litter were pooled into a single sample bag (approximately 25-30 grams of fecal material from the litter). Fecal samples were obtained fresh and if possible were taken directly from the sow or piglet by rectal stimulation and placed in whirl-pak bags. (Note: piglet feces were removed from the crate on a daily basis. However, sow feces was not removed from the crate floor.) Fecal samples were plated for the determination of the presence of strains 3AP4 and LSSA01 through visual inspection of colony morphology. Furthermore, *Bacillus* present in the fecal samples were isolated and screened against *C. perfringens* isolates in vitro to determine if the inhibitive activity of the *Bacillus* were maintained after passage through the gastrointestinal tract. Strains 3AP4 and LSSA01 were detected in the fecal samples of treated sows on d −1 and d 14 and in litters from treated sows on d 5 and d 14, documenting the fecal-oral transfer of strains 3AP4 and LSSA01 from sow to pig.

Laboratory Analyses:

Fecal Sample Assay-Bacillus Plating.

Eleven grams of the fecal sample was weighed and placed into a whirlpak bag. Samples were masticated with 99 mL of peptone (−1 dilution) and were spore treated for 10 minutes at 80° C. A −2 dilution was made with 1.1 mL of the sample in a 9.9 mL tube of peptone as well as −3 and −4 dilutions. The −1 to −4 dilutions were pour-plated in duplicate with Tryptic Soy Agar and incubated at 32° C. for 24 hours. Plates from the treated pigs were counted by hand for strains 3AP4 and LSSA01 strain enumeration.

Fecal Sample Assay—Bacteriocin Screening Assay:

Eleven grams of fecal material was weighed, transferred to a glass tube containing appropriate media for *Bacillus*, and incubated for 24 hours. Following the 24-hour incubation, samples were centrifuged and the supernatant was collected for use in a bacteriocin screening assay. The bacteriocin screening was conducted in a 48 well format, testing inhibition of the supernatant produced by *Bacillus* isolated from fecal material of control and treated sows or pigs against six different strains of *Clostridium perfringens*. The plates were incubated at 37° C. for 24 hours and inhibition of clostridial growth was measured by absorbance using a plate reader.

Results and Discussion:

Enumeration of Strains 3AP4 and LSSA01 Organisms:

*Bacillus* strains 3AP4 and LSSA01 were detected in the fecal samples of treated sows on lactation day −1 and 14, documenting that administration of strains 3AP4 and LSSA01 *Bacillus* in the feed inoculates the sows' feces ranging from $10^5$ to $10^6$ cfu/g of feces (Table 6). Strains 3AP4 and LSSA01 organisms could not be detected in the feces of pigs from treated sows at 3 d of age, however they were present at 5 and 14 d of age at counts ranging from $10^3$ to $10^4$ cfu of strains 3AP4 and LSSA01/g of piglet feces. Detection of *Bacillus* strains 3AP4 and LSSA01 in the feces of sows supplemented with strains 3AP4 and LSSA01 and their piglets documents the transfer of *Bacillus* strains 3AP4 and LSSA01 from sow to piglet through the fecal-oral route of transmission.

Inhibition of *Clostridium perfringens* by Strains 3AP4 and LSSA01 Organisms:

Total *Bacillus* isolated from the feces of sows supplemented with strains 3AP4 and LSSA01 on d −1 of lactation tended to provide greater (P=0.07) inhibition of *C. perfringens* growth than *Bacillus* isolated from the feces of control sows (Table 7). Likewise, *Bacillus* isolated from the feces of 5 d old pigs from Strains 3AP4 and LSSA01 supplemented sows exhibited greater (P=0.01) inhibition of *C. perfringens* growth compared to bacteria isolated from the feces of 5 d old pigs from control sows.

General Conclusions:

These data illustrate the presence of strains 3AP4 and LSSA01 in the feces of supplemented sows and illustrates the transfer of strains 3AP4 and LSSA01 to piglets from litters of supplemented sows. Furthermore, total *Bacillus* growth from the feces of sows supplemented with strains 3AP4 and LSSA01 and their piglets exhibited greater inhibition of *C. perfringens* growth compared to total *Bacillus* cultured from the feces of control sows and their piglets, demonstrating that not only does transfer of *Bacillus* strains 3AP4 and LSSA01 occur, but these strains' effectiveness at inhibiting *C. perfringens* is maintained through the transfer to the piglet.

TABLE 6

Counts of Strains 3AP4 and LSSA01 (CFU/g and log 10 of feces) from sows and respective litters.

| | Lactation | | Strains 3AP4 and LSSA01 supplemented | |
| --- | --- | --- | --- | --- |
| Item | Day | Control | CFU/g | log 10 |
| Sow | | | | |
| Jan. 29, 2007 | −1 | N/D | $1.1 \times 10^6$ | 5.62 |
| Feb. 19, 2007 | 14 | N/D | $3.7 \times 10^5$ | 5.53 |
| Piglets | | | | |
| Jan. 31, 2007 | 3 | N/D | N/D | N/D |
| Feb. 2, 2007 | 5 | N/D | $6.0 \times 10^3$ | 3.11 |
| Feb. 19, 2007 | 14 | N/D | $1.5 \times 10^4$ | 3.97 |

N/D = Not detectable

TABLE 7

Percent growth inhibition of six *Clostridium perfringens* isolates by strains 3AP4 and LSSA01 isolated from fecal samples of sows and their respective litters.

| Item | Lactation Day | Control | Strains 3AP4 and LSSA01 supplemented | P value[a] |
|---|---|---|---|---|
| Sow | | | | |
| Jan. 29, 2007 | −1 | 38.06 | 73.56 | 0.07 |
| Piglets | | | | |
| Feb. 2, 2007 | 5 | 24.37 | 93.13 | 0.01 |

[a]Single degree of freedom contrasts between control and sows supplemented with strains 3AP4 and LSSA01

Example 6

This example shows a decrease in percent scouring litters, improved 15 d piglet body weight, improved piglet ADG, and decrease in sow weight loss. *Bacillus* strains 15AP4 and LSSA01 were used in this study to determine if these strains reduced scours and improved piglet growth performance pre-weaning in a commercial sow herd subclinical for clostridial disease.

*Bacillus* strains 15AP4 and LSSA01 were evaluated as a dried *Bacillus subtilis* fermentation product that was developed to reduce the incidence of disease associated with pathogenic *Clostridium perfringens* and *Clostridium difficile* strains. Previous rectal swabs taken at the research site where this study was conducted indicate that *C. perfringens* and *C. difficile* were present, were susceptible to the 15AP4 and LSSA01 *Bacillus* strain treatments, and may be were contributing to litter mortality, morbidity, and reduced growth rate pre-weaning although the herd was considered subclinical for clostridial disease. This research evaluated if the *Bacillus* strains 15AP4 and LSSA01 reduced scours and enhanced pre-weaning piglet performance.

Experimental Procedures:

Animals. Data were gathered from 71 sows per treatment of mixed parity and genotype. Sows were randomly allotted to one of two treatments, either control or DFM topdressed with *Bacillus* strains 15AP4 and LSSA01 the last five weeks of gestation and throughout lactation.

Treatment Diets: Gestation and lactation diets were devoid of antibiotics, and no supplemental nutrition (creep feed, milk replacer, etc.) was provided to piglets during lactation. Topdress treatments with *Bacillus* strains 15AP4 and LSSA01 were administered once each day to provide each sow with $2.25\times10^9$ cfu of the strain combination each day. Sows were topdressed starting on d-79 of gestation (5 weeks prior to farrowing) and treatment continued throughout lactation.

Litters: Litters were cross-fostered within treatment group within 24 hours after farrowing to a minimum of 10 and maximum of 12 pigs/litter. Litters were individually weighed at standardization and 15 days post-standardization.

Sow Performance and Subsequent Litter Data: Identification number, genotype, parity, replicate number, farrowing date, treatment start date, wean date, date of standardization, and date of litter weight were recorded for each sow on test. Native litter information for each sow was also recorded, including number born alive, stillbirths, and mummies. Sow body condition was determined at standardization and 15 days post-standardization. Body condition was recorded based on a subjective 3-point scale, with 1=thin, 2=desired condition, and 3=overweight.

Scour Scores: The percentage of scouring litters was calculated as the total number of litters identified as scouring/total number of litters per treatment×100. Litters were only considered scouring during the first two days after farrowing if the scours persisted to d 3 post-farrowing to eliminate any consideration of loose stools due to "milk scours" that clear up within the first two days after birth. Each litter was assigned a subjective scour score daily during lactation defined as follows: 0=no scours present in the litter; 1=less than 50% of the litter exhibited signs of scours; 2=More than 50% of the litter exhibited signs of scours.

Experimental Design: Data were analyzed as a randomized complete block design with two treatments and sow (or litter) as the experimental unit using the PROC MIXED procedure of SAS.

Results and Discussion:

Control sows tended (P=0.08) to have more live pigs born than sows supplemented with *Bacillus* strains 15AP4 and LSSA01 (Table 8). Sows allotted to the treatment with *Bacillus* strains 15AP4 and LSSA01 entered the lactation phase with a slightly lower body condition score than control sows but had a higher body condition score 15 d after farrowing, indicating sows supplemented with *Bacillus* strains 15AP4 and LSSA01 lost less weight during the lactation period as evidenced by the significantly lower (P=0.006) change in body condition score value compared to control sows.

TABLE 8

The effect of the DFM supplementation pre-farrowing on litter size and body condition score of sows.

| | | | | | | Body Condition Score[1] | | |
|---|---|---|---|---|---|---|---|---|
| Treatment | n | Parity, n | Live born, n | Still-born, n | Mum., n | d 0 | D 15 | Ch. BCS |
| DFM | 71 | 4.97 | 10.82 | 1.65 | 0.35 | 1.99 | 1.96 | 0.028 |
| Negative control (NC) | 71 | 4.80 | 11.78 | 1.48 | 0.34 | 2.08 | 1.86 | 0.225 |
| Pooled standard error of the mean (SEM) | | 0.17 | 0.57 | 0.68 | 0.11 | 0.05 | 0.06 | 0.058 |
| Significance (P value) | | 0.47 | 0.08 | 0.44 | 0.91 | 0.13 | 0.23 | 0.006 |

[1]Subjective body condition score based on a 3-point scale: 1 = thin; 2 = good; 3 = overweight.

Supplementation with *Bacillus* strains 15AP4 and LSSA01 to sows resulted in a tendency toward a greater (P=0.07) average piglet body weight 15 d after farrowing compared to control sows (Table 9). The improvement in d 15 body weights of pigs born to sows supplemented with *Bacillus* strains 15AP4 and LSSA01 was further supported by a tendency toward greater (P=0.11) ADG compared to control pigs. The coefficient of variation associated with individual piglet body weight within a litter tended to be lower (P=0.06) in litters born to sows supplemented with *Bacillus* strains 15AP4 and LSSA01 compared to control sows at birth (d 0), with this trend remaining evident numerically (P=0.27) 15 d after farrowing.

TABLE 9

The effect of DFM on piglet performance and litter variation.

| Treatment | n | d-0 Pig wt., lbs | d-0 CV, % | Pig d-15 wt., lbs | d-15 CV, % | Pig ADG, lbs/d | Mortality + Morbidity |
|---|---|---|---|---|---|---|---|
| DFM | 71 | 3.62 | 13.34 | 11.99 | 16.38 | 0.54 | 9.62 |
| Negative control (NC) | 71 | 3.55 | 14.45 | 11.50 | 17.27 | 0.51 | 9.75 |
| Pooled standard error of the mean (SEM) | | 0.077 | 0.409 | 0.24 | 0.60 | 0.015 | 1.43 |
| Significance (P value) | | 0.18 | 0.06 | 0.07 | 0.27 | 0.11 | 0.94 |

Supplementation with *Bacillus* strains 15AP4 and LSSA01 decreased (P=0.02) the percentage of scouring litters from 14% to 2.8%, and litters born to sows provided the DFM had lower (P=0.02) average scour scores in the first week after birth compared to control litters (Table 10).

TABLE 10

The incidence of drug treatment and scour in litters reared by sows supplemented DFM 5-weeks prior to farrowing and during a 15-d lactation period.

| Treatment | n | Ave. d0-7 scour score[1] | Litters scouring, %[2] | Litters treated for scours, %[3] | Trts. given in scouring litters, n[4] |
|---|---|---|---|---|---|
| DFM | 71 | 0.012 | 2.81 | 2.82 | 11.0 |
| Negative control (NC) | 71 | 0.069 | 14.08 | 7.04 | 16.4 |
| Significance (P value) | | 0.02 | 0.02 | 0.25 | 0.54 |

[1]Subjective scour score: 0 = no scours; 1 = less than 50% of litter showing scours; 2 = More than 50% of the litter showing signs of scour.
[2]Calculated as the total number of litters identified as scouring/total number of litters per treatment.
[3]Calculated as the number of litters treated for scours (Tylan)/total number of litters per treatment
[4]Average number of Tylan injections given per litter.

Example 7

Introduction:

A *Bacillus*-based direct-fed microbial (DFM) was specifically developed to aid in the prevention of clostridial-related scours in neonatal pigs. In vitro analysis of the effects of the DFM strongly supports its effectiveness against *C. perfringens* and *C. difficile* isolated from scouring piglets. This study was devised to document sow and litter performance responses and decreases in piglet intestinal clostridia counts from the supplementation of the DFM to sows in an asymptomatic herd.

Experimental Procedures:

A total of 208 mixed parity sows (and some gilts) were used for the experiment and were fed one of two dietary treatments during the gestation and lactation periods. One hundred and four sows were fed standard control diets during gestation and lactation, and the additional 104 sows were fed the standard diets supplemented with a DFM including substantially equal CFU counts of *Bacillus* strains LSSA01 and 3AP4 at a 1 lb/ton inclusion level of product containing $7.5 \times 10^8$ CFU/g of both of the strains for six weeks prior to and throughout the lactation period. Treatments were distributed in a randomized complete block design with sows blocked by parity with the average parity being 1.78 for DFM sows and 1.82 for control sows. Pulmotil (and other antibiotics) were excluded from the experimental diets. Lactation length was targeted at 21 days, but lengths from 18 to 25 days were deemed acceptable.

Daily feed intakes are an estimate based on feed drop information. In a previous experiment actual feed drop weight was regressed against calibrated feed drop weight and gave the equation $y = 0.6181x^{1.2357}$ $R^2 = 0.9882$, where y=actual output and X=calibrated drop weight Data collected on their litters included, 1) number born and number born alive, 2) number of stillborns and mummies, 3) number weaned, 4) average piglet weight at birth and weaning, 5) ADG during the lactation period, 6) scour scores, which are presented as a percentage of litters scouring during the first week of age. Scores range from 0 to 5 with 0 being normal and 5 being severe. There were no scores above 2 reported for this study, and 7) pre-weaning mortality.

From the individual piglets, data collected included 1) individual piglet body weights on the last two farrowing groups—litter variation, 2) enumeration of DFM *Bacillus* in the GI tract of piglets at 3 d of age, and 3) enumeration of clostridia in the GI tract of piglets at 3 and 10 d of age. A total of 50 litters (523 piglets) for DFM sows and 48 litters (523 piglets) for control sows were used for data analysis.

One piglet per litter was selected from the litters selected per treatment for sampling on d 3 of age and d 10 of age from each farrowing group. On each sampling day, piglets were euthanized by electrical stunning and exsanguinated for collection of gastrointestinal tissues for bacterial enumeration. Sampling occurred in as many of the four farrowing groups as needed to obtain adequate replication [~15 pigs/treatment for each age (d 3 and d 10)].

Sampling and Dissection: Following euthanization by exsanguination, piglet intestinal samples were dissected to obtain gastrointestinal tissue samples. Specific sections were obtained as follows: The duodenal section for enumeration of clostridia and *Bacillus* counts were ligated at the pyloric junction and 10 cm distally, dissected and placed in a Whirl-Pak bag with ~10 mL of sterile saline. The jejunal sample for clostridia and *Bacillus* enumeration was ligated 40 cm distally from the duodenum end and 20 cm distally from the first ligation, dissected and placed in a Whirl-Pak bag with ~10 mL of sterile saline. The ileal section for clostridia and *Bacillus* enumeration was ligated at the ileal-cecal junction and 15 cm proximally, dissected, and placed in a Whirl-Pak bag with ~10 mL of sterile saline. A section of the distal colon was obtained by ligating the colon section at its connection to the spiral colon and 8 cm distally for clostridia and *Bacillus* enumeration. The ligated section was dissected and placed in a Whirl-Pak bag with ~10 mL of sterile saline. Samples were transported to the Agtech lab on ice for processing.

Enumeration of intestinal *Clostridia* and *Bacillus*. Gastrointestinal samples were plated to enumerate DFM *Bacillus* strains in 3 d old piglets as well as clostridia counts in both 3 and 10 d old piglets in the small and large intestine. Samples were dissected on-farm as described in the previous section. Two dilutions of each intestinal section (duodenum, jejunum, ileum, and large intestine) were plated in duplicate on Tryptic Soy Agar (TSA) for *Bacillus growth* and *C. perfringens* Agar (CPA) for clostridia growth. Each sample was rinsed with sterile peptone to remove intestinal contents, dissected longitudinally, weighed, diluted in 99 mL of peptone and masticated for 60s. After mastication, a 10 ml aliquot was taken from the −1 dilution of each tissue sample and placed in a sterile test tube. Samples were spore treated in a heat block at 70° C. for 30 minutes, after which a subsequent −3 dilution was made. The −1 and −3 dilutions were plated onto TSA for the enumeration of *Bacillus* colonies and onto CPA to determine clostridial counts. The cells from the −1 dilution were pelleted by centrifugation, resuspended in 10 ml of TSB+ 10% glycerol, divided into two aliquots in 15 mL conical tubes, and frozen for subsequent analysis.

Results and Discussion:

Daily feed intake did not differ when comparing control and DFM supplemented sows (Table 11). DFM supplemented sows farrowed more (P>0.05) total pigs and pigs born alive than control sows, although this response is likely a reflection of conception rate that occurred before DFM treatment. Sows supplemented with DFM weaned more pigs (P=0.06) than control sows and, although not significant (P=0.12), this response was reflected in the lower percentage of piglet mortality with DFM supplementation.

TABLE 11

Performance of Sows Supplemented with DFM in Late Gestation and Lactation[1,2,3]

| Treatment | Daily feed intake, lbs[4] | Wean-to-Estrus Interval, d[5] |
|---|---|---|
| DFM | 12.22 | 5.90 |
| Control | 11.99 | 5.60 |
| SEM | 0.37 | 0.60 |
| Level of significance Dietary treatment | 0.54 | 0.55 |

[1]The average parity was 1.78 for DFM sows and 1.82 for control sows.
[2]Feed intake: n = 99 for DFM sows and n = 101 for control sows; Wean-to-estrus interval: n = 91 for DFM sows and n = 95 for control sows.
[3]Outliers defined as any data point plus or minus three standard deviations from the mean.
[4]Average feed intake over lactation period. Daily feed intake is an estimate based on feed drop information (calculator determined in JBS United experiment 07-S025).
[5]There was not effect f lactation length on wean-to-estrus interval.

Piglet performance determined by weighing pigs individually from a subset of 50 litters from DFM supplemented sows and 48 litters from control sows is displayed in Table 12. No differences in piglet performance (weaning weights, ADG, litter size, and mortality) were observed between treatments when analyzing the data from this subset of litters. However, when piglet performance was evaluated based on litter and encompassing the entire dataset from the trial (103 DFM litters and 102 control litters) litters nursing DFM supplemented sows had greater (P=0.02) weaning weights compared to control litters (Table 13). Although initial litter weight was also greater (P=0.01) for litters nursing DFM supplemented sows, the improvement in litter weaning weight was at least partially due to the tendency toward improvement (P=0.09) in litter ADG of DFM litters compared to controls.

TABLE 12

Native Litter Performance of Pigs Nursing Sows Supplemented with DFM in Late Gestation and Lactation.[1,2,3]

| Treatment | Total born | Born alive | Stillborn | Mummies |
|---|---|---|---|---|
| DFM | 13.27 | 12.15 | 1.03 | 0.28 |
| Control | 12.39 | 11.09 | 1.21 | 0.14 |
| SEM | 0.43 | 0.37 | 0.17 | 0.09 |
| Level of significance Dietary treatment | 0.04 | <0.01 | 0.27 | 0.11 |

[1]The average parity was 1.78 for DFM sows and 1.82 for control sows.
[2]Total born: n = 104 for DFM and control sows; Born alive and mummies: n = 103 for DFM and control sows; Stillborn: n = 101 for DFM and control sows;
[3]Outliers defined as any data point plus or minus three standard deviations from the mean.

The high percentage of scouring litters was surprising as the health status of the herd at the time of the trial was considered to be relatively healthy (Table 13). More surprising was the numerically higher (P=0.64) percentage of DFM litters scouring compared to controls, as data from previous trials have consistently reported decreases in the percentage of scouring litters with administration of DFM. Scour severity was also scored on a scale of 0 (no scours) to 5 (severe scours), and none of the litters on test scored above a scour severity score of 2, suggesting these scours were likely transient "milk" scours and not indicative of a major health challenge.

TABLE 13

Standardized Litter Performance (Expressed Per Piglet and Per Litter) of Sows Supplemented with DFM in Late Gestation and Lactation[1,2,3]

| | Per Piglet | | | | | Per Litter | | | | | | |
|---|---|---|---|---|---|---|---|---|---|---|---|---|
| | Initial weight, lbs | Weaning weight, lbs | Gain, lbs | ADG, lbs | Standardized Litter Size | Initial weight, lbs | Weaning weight, lbs | Gain, lbs | ADG, lbs | % Scours[4] | Wean litter size | % mortality |
| DFM | 3.39 | 13.82 | 10.44 | 0.53 | 10.99 | 37.14 | 136.27 | 99.33 | 5.01 | 31.44 | 9.86 | 10.41 |
| Control | 3.09 | 13.43 | 10.41 | 0.52 | 10.95 | 33.97 | 128.76 | 94.91 | 4.74 | 28.66 | 9.56 | 12.76 |
| SEM | 0.12 | 0.25 | 0.25 | 0.01 | 0.06 | 1.28 | 3.15 | 3.21 | 0.16 | 5.86 | 0.16 | 1.54 |
| Level of significance Dietary treatment | 0.01 | 0.11 | 0.88 | 0.56 | 0.54 | 0.01 | 0.02 | 0.17 | 0.09 | 0.64 | 0.06 | 0.12 |

[1]Outliers defined as any data point plus or minus three standard deviations from the mean.
[2]Lactation length ranged from 18 to 25 days.
[3]Growth performance per piglet n = 101 for DFM litters and n = 100 for control litters; Growth performance per litter: n = 103 for DFM pigs and n = 102 for control pigs; Scour scores: n = 104 for DFM and control pigs; Standardized litter size: n = 99 for DFM pigs and n = 98 for control pigs; Mortality: n = 99 for DFM and control pigs.
[4]Percent of litters scouring at least once during wk 1 of age; n = 52 litters for DFM piglets, n = 48 litters for control piglets. Scours were scored on a scale from 0 to 5 with 0 being no scours and 5 being severe scours. There were no observations above a 2 reported for this study.

Figure 4:
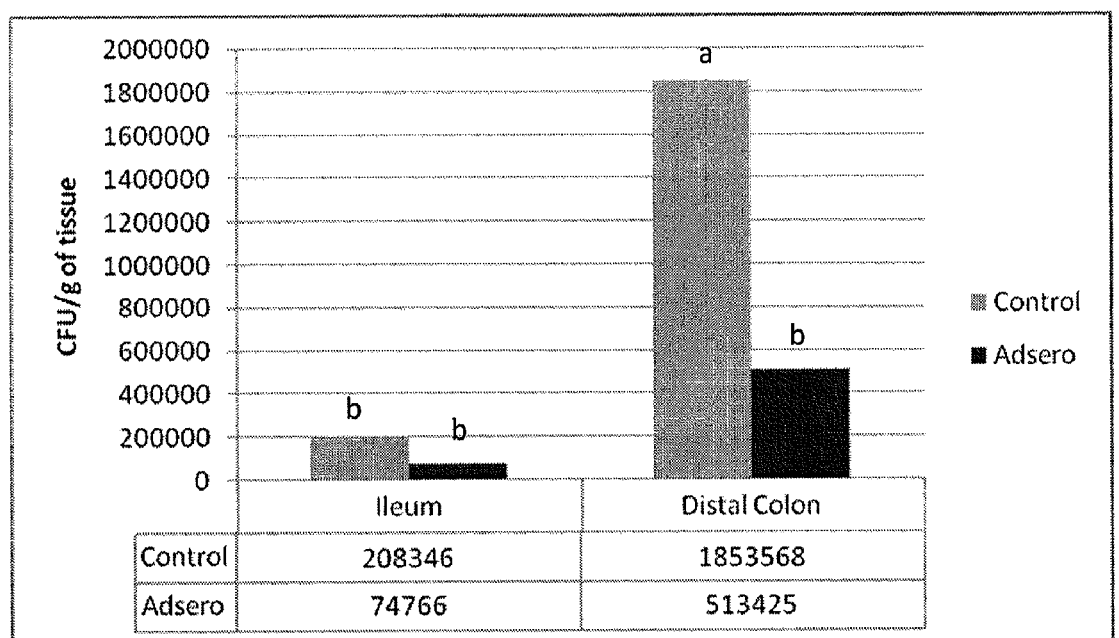

Bacillus organisms from the DFM were not detected in the intestinal tract of piglets sampled at 3 days of age. Intestinal clostridia counts from a combination of ileal and distal colon samples obtained from 3 day old piglets were reduced in piglets nursing DFM supplemented sows compared to control sows ($2.9 \times 10^5$ vs $1.0 \times 10^6 \pm 4.6 \times 10^5$, P=0.07). Although DFM supplementation did not impact clostridia counts in the ileum of piglets at 3 days of age, clostridia counts were reduced (P>0.05) in the distal colon of pigs nursing DFM supplemented sows compared to control pigs (section×treatment interaction, P=0.14; FIG. 4). Although clostridia counts in the intestinal tract of 10 d old pigs nursing DFM supplemented sows were numerically lower compared to control pigs, there was no statistical difference between treatments ($1.5 \times 10^5$ vs. $3.3 \times 10^5 \pm 1.6 \times 10^5$, P=0.27).

In summary, this study demonstrates the benefits of DFM supplementation to sows during gestation and lactation on number of pigs weaned and piglet weight gain in a herd considered to have a subclinical clostridia challenge. Additionally, the DFM decreased the clostridial load in the gastrointestinal tract of 3 day old piglets by specifically decreasing the clostridial load in the large intestine. These data support previous findings in which DFM improved sow and piglet performance in herds without clinical clostridia challenges.

Example 8

Objective:

To determine the efficacy of a direct-fed microbial (DFM) for enhancing sow and piglet performance during lactation in a commercial sow unit considered subclinical for clostridia scours.

Materials and Methods:

Sows (Genetiporc) and their respective litters were evaluated in a 1200-sow commercial swine production facility. At day 72 of gestation (last 6 weeks of gestation), sows were allotted to three treatments by parity group (1 vs. 2+) and 114 day farrowing date. Blocks consisted of three sows of the same parity group. Three treatments were administered to the sows during gestation and lactation: 1) a negative control diet devoid of BMD and a DFM (described below), 2) a positive control diet consisting of the negative control supplemented with BMD, and 3) the negative control diet with DFM supplementation. Feed-grade antibiotics (e.g., CTC, Pulmotil) were not used in the gestation and lactation feeds during the trial period. Also, litters were not treated with oral or injectable antibiotics for the duration of the trial unless there were severe health challenges. If treatments occurred, all individual pig treatments were recorded. Sows were vaccinated two weeks prior to farrowing and treatments were top-dressed one time daily to approximate 250 g/ton BMD and 454 g/ton DFM (Table 14). The DFM included substantially equal CFU counts of Bacillus strains LSSA01 and 3AP4. The DFM top-dress was formulated by combining 10 lb of DFM ($7.5 \times 10^8$ cfu/g product) and 5 lb of cornstarch to provide the equivalent of 1 lb/ton when 1 teaspoon/day was top-dressed, which provided $2.25 \times 10^9$ cfu/day. BMD was top-dressed beginning two weeks prior to lactation until weaning, whereas the DFM was top-dressed beginning six weeks prior to lactation until weaning. To avoid cross-contamination in gestation, sows were grouped together by treatment. A "non-test" sow was placed between treatment groups. Any residual feed from sows that were "off-feed" was removed from the trough prior to watering to prevent contamination.

TABLE 14

Summary of treatments administered, vaccinations, and top-dress procedures performed during the experiment.

| Treatments | Vaccination[1] | BMD[2] | DFM[3] |
|---|---|---|---|
| Negative Control | Yes | No | No |
| Positive Control (BMD) | Yes | 1 scoop/day BMD, last 2 weeks of gestation through weaning | No |
| DFM Top-Dress | Yes | No | 1 teaspoon/day, last 6 weeks of gestation through weaning |

[1]Vaccination included Beacon Scour Block (E-coli-4 + Clostridium perfringens type C) distributed by Newport Laboratories. Gilts were vaccinated 4 and 2 weeks prior to farrowing. Sows were vaccinated 2 weeks prior to farrowing only.
[2]Each scoop was equivalent to 250 g/ton of BMD.
[3]Each teaspoon contained 3 g of DFM and provided $2.25 \times 10^9$ cfu/day. This was equivalent to 454 g of the DFM/ton of feed.

Sows were weighed prior to farrowing and at weaning to determine sow body weight change over the course of the lactation period. Litters were cross-fostered within treatment groups only and to a minimum of 9-10 pigs/litter within the first 24 hours post-farrowing. Scouring litters were recorded to determine the percentage of litters scouring for each treatment, and scouring severity was determined for each litter daily based on visual evaluation using a 0 to 3 scale (0=no scours and 3=heavy scours). The following measurements were recorded for each litter:

Measurements: The following measurements were taken: 1. date farrowed, 2. parity, 3. sow body weight (pre-farrow and weaning), 4. no. pigs at standardization and at weaning, 5. pig removals and reason for removal, 7. individual pig treatments, and 8. scouring litters.

Results and Discussion:

Average parity of sows during the second trial was between 4 and 5 for all three treatment groups (Table 15). Although there was no significant treatment effect (P=0.60), DFM supplemented sows averaged numerically fewer pigs born alive than control sows or those supplemented with BMD. DFM and BMD supplemented sows had lighter (P=0.02) prefarrowing body weights than negative control sows, whereas there was no difference in body weight between the treatments when sows were weighed 16 d into the lactation period. As a result, DFM and BMD supplemented to sows reduced (P=0.08) body weight loss during lactation compared to control sows. Sow weight loss during lactation was also evaluated with prefarrow body weight and live born pigs as covariates in the analysis, and while this altered degrees of significance it did not change interpretation of the data. Percentage of scouring litters and scour severity are not reported, as only one litter was observed to be scouring during the time this trial was conducted.

TABLE 15

Effects of DFM or BMD supplementation to gestating sows prior to farrowing.

| Treatment | N | Parity | Live Born | Prefarrow weight, lbs | d-16 lactation sow weight, lbs | Sow Weight loss, lbs | Sow weight loss, lbs | Sow weight loss, lbs |
|---|---|---|---|---|---|---|---|---|
| DFM (6-wk) | 49 | 4.88 | 10.80 | 544.41 | 509.04 | 35.27 | 36.06 | 36.57 |
| BMD (2-wk) | 49 | 4.40 | 11.45 | 543.52 | 496.38 | 45.12 | 46.04 | 44.60 |
| Negative control (NC) | 52 | 4.79 | 11.20 | 569.23 | 521.36 | 50.35 | 48.53 | 50.25 |
| Covariate | | | | | | — | Prefarrow sow weight | Live Born |
| Pooled standard error of the mean (SEM) | | 0.41 | 0.56 | 13.30 | 12.14 | 6.96 | 6.70 | 6.62 |
| Significance[1] | | 0.65 | 0.60 | 0.08 | 0.19 | 0.08 | 0.16 | 0.12 |
| Treatment | | | | | | | | |
| DFM vs BMD | | 0.39 | 0.32 | 0.95 | 0.37 | 0.18 | 0.17 | 0.26 |
| DFM & BMD vs NC | | 0.73 | 0.88 | 0.02 | 0.11 | 0.08 | 0.21 | 0.09 |

[1]Levels of significance (P-values) accorded to the main effect of treatment and a single degree-of-freedom comparison of DFM and BMD supplementation.

The lack of scouring litters in this second trial documents the varying health status of the herd at the time the two trials were conducted. The herd had just gone through a PRRS break prior to the start of the first trial, whereas the herd was PRRS stable at the time the second trial was conducted.

Conclusion:

These data indicate that BMD and DFM decreased sow weight loss during lactation when herd health status was good and when clinical signs of clostridial scours were not present. This trial and the results of the previous trial described in Example 4 conducted during health challenges (PRRS and scours) indicate a beneficial effect of DFM supplementation regardless of herd health status.

Example 9

Objective:

To determine the optimal level of supplementation with a direct-fed microbial (DFM) in nursery pigs that results in enhanced growth performance.

Materials and Methods:

There were five (5) dietary treatments with twelve (12) replicates per treatment and eight pigs per pen. Pigs were allotted by weight and sex. Sex ratio was equal within each replicate. A basal diet was prepared for each nursery phase. The direct-fed microbial (DFM) included strains 3AP4 and LSSA01 in substantially equal amounts of CFUs. The DFM contained $3.75 \times 10^8$ CPU/g of each strain for a total of $7.5 \times 10^8$ CFU/g of DFM product. Additional ingredients in the DFM product that served as carrier included calcium carbonate and rice hulls. Diets typical of those used in the commercial swine industry were fed during each nursery phase. Five premixes labeled A through E were prepared for each treatment and were used throughout the experiment to prepare each treatment diet. Treatment diets defined below were formulated by blending the appropriate premix into the basal diet at the expense of corn.

The treatments were as follows: control, control diet+0.50 lb of product/ton of feed, control diet+1.00 lb of product/ton of feed, control diet+2.00 lb of product/ton of feed, control diet+4.00 lb of product/ton of feed. The duration of the treatments was 6 weeks, and there were four phases: Phase 1 (6 to 8 d), Phase 2 (1 wk), Phase 3 (1 wk), and Phase 4 (3 wk).

The following measurements were taken: feed samples at time of manufacture, individual pig weights for allotment and weekly pen weights thereafter, feed intakes weekly, mortality and morbidity, medicinal treatments, scour scores, and feed samples collected out of feeders. Scour scores were recorded using the following scale: 1=no scours, 2=any looseness evident in pen, and 3=considerable looseness in pen.

EXCENEL® antibiotic (Pharmacia & Upjohn Co., North Peacock, N.J.) was administered on the day of weaning. Mecadox® antibiotic (Phibro Animal Health, Ridgefield Park, N.J.) was supplemented in the diet during the nursery phases.

Results and Discussion:

Supplementation of DFM to nursery diets resulted in a quadratic (P<0.03) average daily gain (ADG) response during weeks 3 and 5 of the nursery period (Table 14). This improvement in ADG translated to a quadratic increase (P<0.05) in pig body weight at the end of weeks 3, 5, and 6, and pig body weight tended (P<=0.08) to increase linearly during week 4 with DFM supplementation. Average daily feed intake increased quadratically (P<0.02) during week 3, with the greatest feed intake response observed when DFM was supplemented at 0.5 lb/ton. Although the greatest feed intake during week 5 was observed when pigs were fed diets supplemented with 0.5 lb/ton of DFM, the only treatment that differed from the control was a decrease (P<0.05) in feed intake when pigs were supplemented with DFM at the 4 lb/ton inclusion level.

Contrasts comparing the various levels of DFM supplementation that were tested in this study indicated that DFM supplementation at 0.5 and 1 lb/ton of feed resulted in greater (P≦0.05) ADG, average daily feed intake (ADFI) and pig body weight in week 3 when compared to the average responses when DFM was supplemented at higher levels (Table 14). During weeks 4 and 5, supplementation with DFM at 0.5 lb/ton resulted in greater (P≦0.05) ADFI and pig body weight compared to the average of pigs fed DFM supplemented at higher levels, whereas the same was true for ADG and pig body weight when DFM was supplemented at 1 lb/ton in week 5 (P≦0.05). Comparisons of DFM supplementation of 2 lb/ton verses 4 lb/ton tended (P≦0.10) to indicate general decreases in growth performance within weeks 2, 3, 5, and 6 when DFM was supplemented at 4 lb/ton.

Cumulatively over the entire nursery trial, ADG and pig body weight increased quadratically (P<0.05) with increasing DFM supplementation, such that supplementation with 0.5 lb/ton yielded the greatest response (Table 15). Average daily feed intake increased linearly (P=0.05) as DFM supplementation increased with the greatest ADFI occurring in pigs supplemented with DFM at 0.5 lb/ton. Contrasts comparing levels of DFM supplementation in the overall trial indicated ADG and ADFI were greater (P<0.05) when pigs were fed DFM at 0.5 lb/ton compared to DFM supplementation at higher levels. Scour scores were generally low in this study, indicating minimal enteric challenge, and were not impacted by DFM supplementation (Table 15).

In conclusion, DFM supplementation during the nursery period improved growth performance in the middle and later nursery phases, as well as over the cumulative trial. These improvements were evidenced when DFM was supplemented at the 0.5 and 1.0 lb/ton inclusion level. Specifically, DFM supplemented at 0.5 or 1.0 lb/ton improved ADG as a result of increased ADFI, and culminated in an approximately 1 lb heavier pig at the end of the nursery period.

TABLE 14

Efficacy of graded levels of DFM on weekly growth performance in nursery pigs[1]

| | Treatment | | | | | Pooled standard error of the mean (SEM) | Contrast P-values | | | 0.5 lbs/ton vs. higher | 1.0 lbs/ton vs. higher | 2.0 lbs/ton vs. 4.0 lbs/ton |
|---|---|---|---|---|---|---|---|---|---|---|---|---|
| | 1 | 2 | 3 | 4 | 5 | | Diet P-value | Linear | Quadratic | | | |
| | DFM (lbs/ton) | | | | | | | | | | | |
| | 0 | 0.5 | 1.0 | 2.0 | 4.0 | | | | | | | |
| Week 1 | | | | | | | | | | | | |
| Start wt. (lbs) | 15.37 | 15.38 | 15.44 | 15.42 | 15.30 | 0.515 | 0.412 | 0.516 | 0.096 | 1.00 | 0.236 | 0.118 |
| End wt. (lbs) | 16.05 | 16.03 | 15.94 | 16.07 | 15.69 | 0.584 | 0.649 | 0.280 | 0.502 | 0.562 | 0.797 | 0.186 |
| ADG (lb) | 0.10 | 0.09 | 0.07 | 0.09 | 0.06 | 0.026 | 0.813 | 0.375 | 0.806 | 0.596 | 0.949 | 0.338 |
| ADFI (lb) | 0.19 | 0.18 | 0.17 | 0.19 | 0.16 | 0.016 | 0.553 | 0.431 | 0.902 | 0.988 | 0.604 | 0.187 |
| F/G (lb/lb) | 1.90 | 2.00 | 2.43 | 2.11 | 2.67 | 0.870 | 0.325 | 0.359 | 0.665 | 0.295 | 0.209 | 0.363 |
| Week 2 | | | | | | | | | | | | |
| End wt. (lbs) | 21.07 | 21.16 | 20.91 | 21.27 | 20.51 | 0.753 | 0.443 | 0.298 | 0.340 | 0.454 | 0.955 | 0.084 |
| ADG (lb) | 0.72 | 0.74 | 0.73 | 0.74 | 0.69 | 0.036 | 0.541 | 0.384 | 0.204 | 0.432 | 0.650 | 0.137 |
| ADFI (lb) | 0.74 | 0.75 | 0.74 | 0.76 | 0.70 | 0.035 | 0.362 | 0.240 | 0.210 | 0.443 | 0.687 | 0.064 |
| F/G (lb/lb) | 1.03 | 1.03 | 1.02 | 1.03 | 1.03 | 0.027 | 0.995 | 0.967 | 0.712 | 1.00 | 0.717 | 0.981 |
| Week 3 | | | | | | | | | | | | |
| End wt. (lbs) | 27.53[ab] | 28.18[a] | 27.88[a] | 27.43[ab] | 26.61[b] | 0.909 | 0.037 | 0.025 | 0.023 | 0.039 | 0.051 | 0.109 |
| ADG (lb) | 0.902[ab] | 0.968[a] | 0.949[a] | 0.858[b] | 0.858[b] | 0.054 | 0.004 | 0.014 | 0.028 | 0.007 | 0.004 | 1.000 |
| ADFI (lb) | 1.15[ac] | 1.23[b] | 1.18[ab] | 1.12[ac] | 1.08[c] | 0.060 | 0.003 | 0.004 | 0.015 | 0.001 | 0.016 | 0.302 |
| F/G (lb/lb) | 1.29 | 1.27 | 1.24 | 1.32 | 1.27 | 0.031 | 0.418 | 0.899 | 0.751 | 0.804 | 0.150 | 0.196 |
| Week 4 | | | | | | | | | | | | |
| End wt. (lbs) | 36.00[ab] | 37.03[b] | 36.27[ab] | 35.64[ab] | 35.00[b] | 1.138 | 0.216 | 0.081 | 0.160 | 0.059 | 0.202 | 0.450 |
| ADG (lb) | 1.03 | 1.11 | 1.05 | 1.01 | 1.05 | 0.049 | 0.412 | 0.679 | 0.630 | 0.103 | 0.680 | 0.438 |
| ADFI (lb) | 1.50 | 1.60 | 1.53 | 1.46 | 1.51 | 0.070 | 0.192 | 0.336 | 0.524 | 0.044 | 0.331 | 0.347 |
| F/G (lb/lb) | 1.47 | 1.45 | 1.46 | 1.45 | 1.44 | 0.026 | 0.932 | 0.506 | 0.993 | 0.885 | 0.623 | 0.777 |
| Week 5 | | | | | | | | | | | | |
| End wt. (lbs) | 45.07[ab] | 46.28[a] | 45.80[a] | 44.73[ab] | 43.19[b] | 1.334 | 0.039 | 0.022 | 0.026 | 0.049 | 0.038 | 0.128 |
| ADG (lb) | 1.30[a] | 1.33[a] | 1.33[a] | 1.28[a] | 1.18[b] | 0.041 | 0.025 | 0.014 | 0.020 | 0.132 | 0.019 | 0.053 |
| ADFI (lb) | 1.91[ab] | 1.97[a] | 1.90[ab] | 1.84[bc] | 1.78[c] | 0.054 | 0.034 | 0.006 | 0.166 | 0.012 | 0.091 | 0.324 |
| F/G (lb/lb) | 1.49 | 1.49 | 1.44 | 1.45 | 1.52 | 0.026 | 0.197 | 0.795 | 0.047 | 0.506 | 0.160 | 0.065 |
| Week 6 | | | | | | | | | | | | |
| End wt. (lbs) | 55.56[ab] | 56.69[a] | 56.40[a] | 55.66[ab] | 53.57[b] | 1.60 | 0.134 | 0.082 | 0.044 | 0.170 | 0.106 | 0.102 |
| ADG (lb) | 1.50 | 1.51 | 1.51 | 1.53 | 1.44 | 0.055 | 0.670 | 0.517 | 0.267 | 0.809 | 0.616 | 0.159 |

TABLE 14-continued

Efficacy of graded levels of DFM on weekly growth performance in nursery pigs[1]

| | Treatment | | | | | Pooled standard error of the mean (SEM) | Contrast P-values | | | 0.5 lbs/ton vs. higher | 1.0 lbs/ton vs. higher | 2.0 lbs/ton vs. 4.0 lbs/ton |
|---|---|---|---|---|---|---|---|---|---|---|---|---|
| | 1 | 2 | 3 | 4 | 5 | | Diet P-value | Linear | Quadratic | | | |
| | | DFM (lbs/ton) | | | | | | | | | | |
| | 0 | 0.5 | 1.0 | 2.0 | 4.0 | | | | | | | |
| ADFI (lb) | 2.24 | 2.31 | 2.29 | 2.24 | 2.18 | 0.082 | 0.651 | 0.342 | 0.242 | 0.350 | 0.285 | 0.536 |
| F/G (lb/lb) | 1.49 | 1.53 | 1.51 | 1.47 | 1.52 | 0.020 | 0.281 | 0.812 | 0.964 | 0.213 | 0.424 | 0.109 |

[1]There were 12 replicates pens per dietary treatment.
[a-c]Means with different superscripts within a row are significantly different (P < 0.05)

TABLE 15

Efficacy of graded levels of DFM on cumulative growth performance and scour scores in nursery pigs[1,2,3]

| | Treatment | | | | | Pooled standard error of the mean (SEM) | Contrast P-values | | | 0.5 lbs/ton vs. higher | 1.0 lbs/ton vs. higher | 2.0 lbs/ton vs. 4.0 lbs/ton |
|---|---|---|---|---|---|---|---|---|---|---|---|---|
| | 1 | 2 | 3 | 4 | 5 | | Diet P-value | Linear | Quadratic | | | |
| | | DFM (lbs/ton) | | | | | | | | | | |
| | 0 | 0.5 | 1.0 | 2.0 | 4.0 | | | | | | | |
| Cumulative | | | | | | | | | | | | |
| Start wt. (lbs) | 15.37 | 15.38 | 15.44 | 15.42 | 15.30 | 0.515 | 0.412 | 0.516 | 0.096 | 1.00 | 0.236 | 0.118 |
| End wt. (lbs) | 55.56[ab] | 56.69[a] | 56.40[a] | 55.66[ab] | 53.57[b] | 1.60 | 0.134 | 0.082 | 0.044 | 0.170 | 0.106 | 0.102 |
| ADG (lb) | 0.91[ab] | 0.95[a] | 0.93[a] | 0.91[ab] | 0.88[b] | 0.033 | 0.094 | 0.065 | 0.043 | 0.047 | 0.132 | 0.171 |
| ADFI (lb) | 1.27[ab] | 1.33[a] | 1.29[ab] | 1.26[ab] | 1.23[b] | 0.046 | 0.097 | 0.050 | 0.113 | 0.019 | 0.186 | 0.442 |
| F/G (lb/lb) | 1.40 | 1.40 | 1.38 | 1.38 | 1.41 | 0.009 | 0.174 | 0.790 | 0.066 | 0.283 | 0.382 | 0.050 |
| Scour Scores | | | | | | | | | | | | |
| Week 1 score | 1.36 | 1.39 | 1.51 | 1.62 | 1.40 | 0.104 | 0.352 | 0.328 | 0.193 | 0.290 | 1.000 | 0.137 |
| Overall score | 1.14 | 1.11 | 1.18 | 1.14 | 1.13 | 0.030 | 0.530 | 0.921 | 0.665 | 0.192 | 0.244 | 0.856 |

[1]There were 12 replicates pens per dietary treatment.
[2]Scour scores can were recorded as 1 = no scours; 2 = moderate looseness; 3 = considerable looseness.
[3]Pigs were fed dietary treatments from weaning to 42 d post-wean.
[a-b]Means with different superscripts within a row are significantly different (P < 0.05).

It is understood that the various preferred embodiments are shown and described above to illustrate different possible features described herein and the varying ways in which these features may be combined. Apart from combining the different features of the above embodiments in varying ways, other modifications are also considered to be within the scope described herein. The invention is not intended to be limited to the preferred embodiments described above, but rather is intended to be limited only by the claims set out below. Thus, the invention encompasses all alternate embodiments that fall literally or equivalently within the scope of these claims.

What is claimed is:

1. A method comprising administering to a pig an effective amount to inhibit *Clostridium* in litters borne to the pig of at least two *Bacillus* strains selected from strains 22CP1 (ATCC PTA-6508), 3AP4 (ATCC PTA-6506), 15AP4 (ATCC PTA-6507), 2084 (NRRL B-50013), LSSAO1 (NRRL B-50104), and 27 (NRRL B-50105), wherein at least one strain is LSSAO1 (NRRL B-50104).

2. The method of claim 1, wherein the *Bacillus* strains are strains 3AP4 (ATCC PTA-6506) and LSSAO1 (NRRL B-50104).

3. The method of claim 1, wherein the *Bacillus* strains are strains 15AP4 (ATCC PTA-6507) and LSSA01 (NRRL B-50104).

4. The method of claim 1, wherein the *Bacillus* strain is administered to female breeding stock.

5. The method of claim 1, wherein the *Bacillus* strain is administered during gestation of the pig.

6. The method of claim 5, wherein a total microbial count of $3.75 \times 10^5$ CFU/g of feed/day is administered.

7. The method of claim 1, wherein the *Bacillus* strain is administered during lactation of the pig.

8. The method of claim 7, wherein a total microbial count of $8.5 \times 10^8$ CFU/g of feed/day is administered.

9. The method of claim 1, wherein the *Clostridium* is *Clostridium perfringes*.

10. The method of claim 1, wherein the *Clostridium* is *Clostridium difficile*.

11. The method of claim 1, further comprising modifying the *Bacillus* strains administered based on a change in *Clostridium* strains to which the pig is exposed.

12. The method of claim 1, wherein administration of the *Bacillus* strains provides at least one of the following in litters borne to the pig relative to that in litters borne to pigs that have not been administered the *Bacillus* strains: (A) lower average scour scores in the first week after birth, and (B) a decrease in the percentage of scouring litters.

13. The method of claim 1, wherein the pig is in a herd lacking symptoms of *Clostridium infection*.

14. The method of claim 13, wherein administration of the *Bacillus* strains decreases clostridial load in the gastrointestinal tract of piglets borne by the pig relative to that in piglets borne to pigs that have not been administered the *Bacillus* strains.

15. The method of claim 1, wherein the pig is in a unit of pigs that are subclinical for clostridial scours.

16. The method of claim 15, wherein performance of at least one of the pig and piglets borne by the pig is improved during lactation relative to pigs and piglets that have not been administered the *Bacillus* strains.

17. The method of claim 1, wherein the *Bacillus* strain is administered when the pig is at least one of a nursery pig and a feedlot pig.

18. A method comprising administering to a pig an effective amount to inhibit *Clostridium* in litters borne to the pig of *Bacillus* strains 3AP4 (ATCC PTA-6506) and LSSAO1 (NRRL B-50104).

19. The method of claim 18, wherein the pig is a gestating pig.

20. The method of claim 18, wherein the pig is a lactating pig.

21. A method comprising administering to a pig an effective amount to inhibit *Clostridium* in litters borne to the pig of at least two *Bacillus* strains having all of the identifying characteristics of at least two strains selected from strains 22CP1 (ATCC PTA-6508), 3AP4 (ATCC PTA-6506), 15AP4 (ATCC PTA-6507), 2084 (NRRL B-50013), LSSAO1 (NRRL B-50104), and 27 (NRRL B-50105), wherein at least one *Bacillus* strain has all of the identifying characteristics of LSSAO1 (NRRL B-50104).

22. The method of claim 21, wherein the *Bacillus* strains have all of the identifying characteristics of strains 3AP4 (ATCC PTA-6506) and LSSAO1 (NRRL B-50104).

23. The method of claim 21, wherein the *Bacillus* strains have all of the identifying characteristics of strains 15AP4 (ATCC PTA-6507) and LSSA01 (NRRL B-50104).

* * * * *